(12) United States Patent  (10) Patent No.: US 8,349,309 B2
Santerre et al.  (45) Date of Patent: Jan. 8, 2013

(54) POLYMERIC COUPLING AGENTS AND PHARMACEUTICALLY-ACTIVE POLYMERS MADE THEREFROM

(75) Inventors: J. Paul Santerre, Whitby (CA); Mei Li, Toronto (CA)

(73) Assignee: Interface Biologics Inc., Toronto (CA)

( * ) Notice: Subject to any disclaimer, the term of this patent is extended or adjusted under 35 U.S.C. 154(b) by 0 days.

(21) Appl. No.: 12/793,475

(22) Filed: Jun. 3, 2010

(65) Prior Publication Data

US 2011/0112259 A1 May 12, 2011

Related U.S. Application Data

(63) Continuation of application No. 11/129,358, filed on May 16, 2005, now abandoned, which is a continuation-in-part of application No. 10/875,550, filed on Jun. 25, 2004, now abandoned.

(30) Foreign Application Priority Data

May 14, 2004  (CA) ..................................... 2467321

(51) Int. Cl.
*A61K 31/00* (2006.01)

(52) U.S. Cl. ................. 424/78.3; 424/78.08; 424/78.17; 424/78.35; 424/78.37

(58) Field of Classification Search ........................ None
See application file for complete search history.

(56) References Cited

U.S. PATENT DOCUMENTS

| | | | |
|---|---|---|---|
| 4,024,871 | A | 5/1977 | Stephenson |
| 4,532,316 | A | 7/1985 | Henn |
| 4,833,215 | A | 5/1989 | Jedlinski et al. |
| 4,916,193 | A | 4/1990 | Tang et al. |
| 5,321,099 | A | 6/1994 | Goldwasser et al. |
| 5,387,598 | A | 2/1995 | Rossignol |
| 5,578,621 | A | 11/1996 | Rossignol |
| 5,798,115 | A | 8/1998 | Santerre et al. |
| 5,856,348 | A | 1/1999 | Rossignol |
| 5,859,038 | A | 1/1999 | Rossignol |
| 5,886,013 | A | 3/1999 | Rossignol |
| 5,965,590 | A | 10/1999 | Rossignol |
| 5,968,961 | A | 10/1999 | Rossignol |
| 6,020,353 | A | 2/2000 | Rossignol |
| 6,051,576 | A | 4/2000 | Ashton et al. |
| 6,096,525 | A | 8/2000 | Patnaik |
| 6,117,894 | A | 9/2000 | Rossignol |
| 6,127,507 | A | 10/2000 | Santerre |
| 6,299,604 | B1 | 10/2001 | Ragheb et al. |
| 6,344,035 | B1 | 2/2002 | Chudzik et al. |
| 6,602,915 | B2 | 8/2003 | Uhrich |
| 6,689,350 | B2 * | 2/2004 | Uhrich ........................ 424/78.17 |
| 6,703,037 | B1 | 3/2004 | Hubbell et al. |
| 6,770,725 | B2 | 8/2004 | Santerre |
| 2003/0035787 | A1 | 2/2003 | Uhrich |
| 2003/0118528 | A1 * | 6/2003 | Walters et al. .................. 424/59 |
| 2003/0158598 | A1 | 8/2003 | Ashton et al. |
| 2004/0087664 | A1 | 5/2004 | Marcus et al. |
| 2005/0031577 | A1 | 2/2005 | Uhrich |
| 2005/0070470 | A1 * | 3/2005 | Coy et al. ........................ 514/12 |

FOREIGN PATENT DOCUMENTS

| | | |
|---|---|---|
| CA | 2461099 | 4/2003 |
| CA | 2467321 | 11/2005 |
| WO | WO 95/20567 | 8/1995 |
| WO | WO 95/28393 | 10/1995 |
| WO | WO 97/29778 | 8/1997 |
| WO | WO 98/50035 | 11/1998 |
| WO | WO 99/12990 | 3/1999 |
| WO | WO 02/09768 | 2/2002 |
| WO | WO 03/028527 | 4/2003 |
| WO | WO 2004/016214 | 2/2004 |

OTHER PUBLICATIONS

Odian (Principles of Polymerization, 4th ed.(2004).*
http://en.wikipedia.org/wiki/Step-growth_polymerization.*
Yang et al. (Biomacromolecules 2001, 2, 134-141).*
First Examination Report pertaining to Indian Application No. 4579/CHENP/2006 dated Jul. 17, 2012.
Bach et al., "Retention of Antibacterial Activity and Bacterial Colonization of Antiseptic-Bonded Central Venous Catheters," *J. Antimicrob. Chemother*. 37:315-322 (1996).
Budavari, *The Merck Index—Fourteenth Edition* Merck Research Laboratories. Whitehouse Station, NJ, 2006, pp. 1306-1307. Coessens et al., "Synthesis and In Vitro Stability of Macromolecular Prodrugs of Norfloxacin," *J. Cont. Release* 47:283-291 (1997).
DiTizio et al., "A Liposomal Hydrogel for the Prevention of Bacterial Adhesion to Catheters," *Biomaterials* 19:1877-1884 (1998).
Ghosh, "Monomers and Polymers from Nalidixic Acid—Synthesis, Characterization, and Hydrolysis Study," in *Progress in Biomedical Polymers*, Ed. Gebekin et al., Plenum Press, New York, pp. 335-345 (1990).
Ghosh, "Studies Directed Towards Polymeric Quinloone Antibiotics—Synthesis of Potential Monomers From Nalidixic Acid," *Polymeric Mat. Sci. Engin.* 59:790-793 (1988).

(Continued)

*Primary Examiner* — James Rogers
(74) *Attorney, Agent, or Firm* — Clark & Elbing LLP; Kristina Bieker-Brady

(57) ABSTRACT

A pharmaceutically-active polymeric compound of the general formula (I),

Y-[Y$_n$-LINK B-X]$_m$-LINK B  (I)

wherein (i) X is a coupled biological coupling agent of the general formula (II)

Bio-LINK A-Bio  (II)

wherein Bio is a biologically active agent fragment or precursor thereof linked to LINK A through a hydrolysable covalent bond; and LINK A is a coupled central flexible linear first segment of <2000 theoretical molecular weight linked to each of said Bio fragments;
(ii) Y is LINK B-OLIGO; wherein
 (a) LINK B is a coupled second segment linking one OLIGO to another OLIGO and an OLIGO to X or precursor thereof; and
 (b) OLIGO is a short length of polymer segment having a molecular weight of less than 5,000 and comprising less than 100 monomeric repeating units;
(iii) m is 1-40; and
(iv) n is selected from 2-50. The compounds are useful as biomaterials, particularly, providing antibacterial activity in vivo. Also provided are biological coupling agents useful as intermediates in the preparation of the pharmaceutically-active polymeric compounds.

13 Claims, 21 Drawing Sheets

OTHER PUBLICATIONS

Modak et al., "A New Method for the Direct Incorporation of Antibiotic in Prosthetic Vascular Grafts," *Surg. Gynecol. Obstet.* 164:143-147 (1987).

Nathan et al., "Copolymers of Lysine and Polyethylene Glycol: A New Family of Functionalized Drug Carriers," *Bioconjug. Chem.* 4:54-62 (1993).

Roseeuw et al., "Polymeric Prodrugs of Antibiotics with Improved Efficiency," *J. Mater. Sci. Mater. Med.* 10:743-746 (1999).

Woo et al., "Biological Characterization of a Novel Biodegradable Antimicrobial Polymer Synthesized with Fluoroquinolones," *J. Biomat. Res.* 59:35-45 (2001).

Woo et al., "Synthesis and Characterization of a Novel Biodegradable Antimicrobial Polymer," *Biomaterials* 21:1235-1246 (2000).

International Search Report for PCT/CA2005/000742 dated Jul. 21, 2005.

International Preliminary Report on Patentability for PCT/CA2005/000742 dated Nov. 14, 2006.

Office Action pertaining to U.S. Appl. No. 11/129,358, mailed Mar. 13, 2009.

Final Office Action pertaining to U.S. Appl. No. 11/129,358, mailed Dec. 3, 2009.

Supplementary European Search Report pertaining to European Patent Application No. 05746912.4-1216, dated Mar. 9, 2011.

Japanese Notice of Reasons for Rejection pertaining to Japanese Patent Application No. 2007-511817, dated Jul. 13, 2011 (English language translation).

European Patent Office Communication pertaining to European Patent Application No. 05746912.4-1216, dated Nov. 21, 2011.

Examination Report pertaining to Canadian Patent Application No. 2,467,321, dated Jun. 7, 2012.

Examination Report pertaining to Canadian Patent Application No. 2,571,320, dated Jun. 7, 2012.

\* cited by examiner

POLYMERIC COUPLING AGENTS AND PHARMACEUTICALLY-ACTIVE POLYMERS MADE THEREFROM

CROSS REFERENCE TO RELATED APPLICATION

This application is a continuation of U.S. application Ser. No. 11/129,358, filed May 16, 2005, now abandoned, which is a continuation-in-part of U.S. application Ser. No. 10/875,550, filed Jun. 25, 2004, now abandoned, and which claims priority benefit of Canadian Patent Application No. 2,467,321, filed May 14, 2004.

FIELD OF THE INVENTION

This invention relates to polymeric coupling agents as intermediates, pharmaceutically-active polymers made therefrom, composition comprising said polymers and shaped articles made therefrom.

BACKGROUND TO THE INVENTION

It has become common to utilize implantable medical devices for a wide variety of medical conditions, e.g., drug infusion and hemodialysis access. However, medical device implantation often comes along with the risk of infections (1), inflammation (2), hyperplasia (3), coagulation (4). It is therefore important to design such materials to provide enhanced biocompatibility. Biocompatibility is defined as the ability of a material to perform with an appropriate host response in a specific application. The host relates to the environment in which the biomaterial is placed and will vary from being blood, bone, cartilage, heart, brain, etc. Despite the unique biomedical related benefits that any particular group of polymers may possess, the materials themselves, once incorporated into the biomedical device, may be inherently limited in their performance because of their inability to satisfy all the critical biocompatibility issues associated with the specific application intended. For instance while one material may have certain anti-coagulant features related to platelets it may not address key features of the coagulation cascade, nor be able to resist the colonization of bacteria. Another material may exhibit anti-microbial function but may not be biostable for longterm applications. The incorporation of multi-functional character in a biomedical device is often a complicated and costly process which almost always compromises one polymer property or biological function over another, yet all blood and tissue contacting devices can benefit from improved biocompatibility character. Clotting, toxicity, inflammation, infection, immune response in even the simplest devices can result in death or irreversible damage to the patient. Since most blood and tissue material interactions occur at the interface between the biological environment and the medical device, the make-up of the outer molecular layer (at most the sub-micron layer) of the polymeric material is relevant to the biological interactions at the interface. This is a particularly challenging problem for biodegradable polymer systems when a continuous exposure of new surfaces through erosion of the bulk polymer requires a continuous renewal of biocompatible moieties at the surface.

Bioactive agents containing polymer coatings have been developed to improve the biocompatibility of medical device surfaces. Patnaik et al. (5) described a method of attaching bioactive agents, such as heparin (an anti-coagulant) to polymeric substrates via a hydrophilic, isocyanate/amine-terminated spacer in order to provide a coating of the bio-active material on the medical device. The investigator found that the bioactive agent's activity was achieved when the spacer group had a molecular weight of about 100-10,000 daltons. But most preferably that is of 4000 daltons. Unfortunately, such a material would only be applicable for substrates which were not intended to under go biodegradation and exchange with new tissue integration since the heparin in limited to surface and does not form the bulk structure of the polymer chains.

Another example of biomaterial design relates to infection control. In the last decade, a number of strategies have been used in attempts to solve problems such as those associated with medical device infection. One approach is to provide a more biocompatible implantable device to reduce the adhesion of bacteria. Silver coated catheters have been used to prevent exit site infections associated with chronic venous access (6) and peritoneal dialysis (7). However, longterm studies have failed to demonstrate a significant reduction in the number or severity of exit site infections. In addition, bacterial resistance to silver can develop over time and carries with it the risk of multiple antibiotic resistances (8).

Since bacteria adhesion is a very complex process, complete prevention of bacteria adhesion is difficult to achieve with only a passive approach. There remains a need for local controlled drug delivery. The advantages for the latter approach include 1) a high and sustained local drug concentration can be achieved without the systemic toxicity or side effects which would be experienced from systemic doses sufficient to obtain similar local drug concentration; 2) high local drug concentration can be attained, even for agents that are rapidly metabolized or unstable when employed systemically; 3) some forms of site-specific delivery have the potential to establish and maintain local drug action, either by preventing its efflux from the arterial wall or by using vehicles or agents that have a prolonged duration of action; 4) it gives the potential for designing a smart drug delivery system, which can be triggered to start the release and/or modulate the rate of release according to the infection status.

Methods for obtaining compositions which contain drugs and polymers in a composite form to yield bioactive agent release coatings are known. For example, Chudzik et al. (9) formulated a coating composite that contained a bioactive agent (e.g. a drug) and two polymers, i.e., poly(butyl methacrylate) and poly(ethylene-co-vinyl acetate). The coating formed from the above formulation provided good durability and flexibility as well as significant drug release, which could be particularly adapted for use with devices that undergo significant flexion and/or expansion in the course of their delivery and/or use, such as stents and catheters. These approaches have the benefit of localized delivery at high drug concentration, but are unable to keep a sustained and controlled release of drug for long periods. Ragheb et al. (10) found a method for the controlled release of a bioactive agent from polymer coatings. Wherein, two coating layers of polymer were applied to a medical device. The first layer of the device is an absorbent material such as parylene derivatives. Drug or bioactive agent is deposited over at least a portion of this layer. The second biocompatible polymer layer on top of the drug and the first layer must be porous. The polymer is applied by vapor deposition or by plasma deposition. Since the drug release mechanism is totally controlled by porous sizes, making a suitable porous size distribution in the second layer in order to satisfy the required release model is often a technical challenge. As well, this type of system requires multiple processing steps which increases production cost and adds to the need for QA/QC steps.

In addition to the traditional diffusion-controlled delivery systems described in the above references, there exist several more sophisticated in situ drug delivery polymers which can alter the efficacy of drugs by improving target delivery and changing the control parameters of the delivery rate. These include biodegradable hydrogels (11), polymeric liposomes (12), bioresorbable polymers (13) and polymer drugs (14-16). Polymer drugs contain covalently attached pharmaceutical agents on the polymer chain as pendent groups, or even incorporated into the polymer backbone. For example, Nathan et al (17) conjugated penicillin V and cephradine as pendant antibiotics to polyurethanes. Their work showed that hydrolytically labile pendant drugs were cleaved and exhibited antimicrobial activities against *S. aureus, E. faecalis* and *S. pyogenes*.

Ghosh et al. (18) coupled nalidixic acid, a quinolone antibiotic, in a pendant manner to an active vinyl molecule. These vinyl groups can then be polymerized to generate a polymer with pendent antibiotics on each monomer. However, having such pendant groups will dramatically alter the physical structure of the polymer. A better strategy would be to have the drugs within the linear backbone portion of the polymer. In in-vivo hydrolysis studies they reported a 50% release of drug moieties over the first 100 hours. This quinolone drug has been shown to be effective against gram negative bacteria in the treatment of urinary track infections, however chemical modifications of the latter (e.g. ciprofloxacin, norfloxacin and others) have a wider spectrum of activity. More recent work on the conjugation of norfloxacin to mannosylated dextran has been reported. This was driven in an effort to increase the drug's uptake by cells, enabling them to gain faster access to micro-organisms (19). The studies showed that norfloxacin could be released from a drug/polymer conjugate by enzyme media and in vivo studies, the drug/polymer conjugate was effective against *Mycobacterium tuberculosis* residing in liver (20). In the system, norfloxacin was attached pendant to sequences of aminoacids which permitted its cleavage by the lysosomal enzyme, cathepsin B.

Santerre (13a) describes the synthesis and use of novel materials to which when added to polymers converts the surface to have bioactive properties, while leaving the bulk properties of the polymer virtually intact. Applications are targeted for the biomedical field. These materials are oligomeric fluorinated additives with pendant drugs that are delivered to the surface of bulk polymers during processing by the migration of the fluorine groups to the air/polymer interface. These materials can deliver a large array of drugs, including anti-microbials, anti-coagulants and anti-inflammatory agents, to the surface. However modification is limited to the surface. This becomes a limitation in a biodegradable polymer which may require sustained activity throughout the bio-erosion process of the polymer.

Santerre and Mittleman (14) teach the synthesis of polymeric materials using pharmacologically-active agents as one of the co-monomers for polymers. Wherein, 1,6-diisocyanatohexane and/or 1,12-diisocyanatododecane monomers or their oligomeric molecules are reacted with the antimicrobial agent, ciprofloxacin, to form drug polymers. The pharmacologically-active compounds provide enhanced long term anti-inflammatory, anti-bacterial, anti-microbial and/or anti-fungal activity. However, since the reactivities of the carboxylic acid group and the secondary amine group of ciprofloxacin with the isocyanate groups are different, the reaction kinetics become challenging. As well, formulations must be selective in order to minimize strong van der Waals interactions between the drug components and hydrogen bonding moieties of the polymer chains since this can delay the effective release of drug. Hence, an improvement over the latter system are biomonomers made up of the drugs and agents which, without being bound by theory, would ensure a less restricted access of the drug during hydrolysis of the polymer, as well as providing more uniform chemical function for reaction with the isocyanate groups or other monomer reagents.

PUBLICATIONS (1) Mittelman, M W, "Adhesion to biomaterials" in *Bacterial Adhesion*: Molecular and Ecological diversity, M Fletcher (ed) 89-127, 1996)
(2) John F. Burke, et al., "Applications of materials in medicine and dentistry", in Biomaterials Science, 1996, Ch. 7, pp 283-297.
(3) Martin R. Bennett, Michael O'Sullivan, "Mechanism of angioplasty and stent restenosis: implications for design of rational therapy", Pharmacology & Therapeutics 91 (2001) pp 149-166.
(4) Eberhart, R. C., and C. P. Clagett, "Platelets, catheters, and the vessel wall; catheter coatings, blood flow, and biocompatibility", Seminars in Hematology, Vol. 28, No. 4, Suppl. 7, pp 42-48 (1991).
(5) U.S. Pat. No. 6,096,525—Patnaik, B K. Aug. 1, 2000
(6) Groeger J. S. et al., 1993, Ann. Surg. 218:206-210.
(7) Mittelman M. W., et. al., 1994. Ann. Conf. Peritoneal Dialysis, Orlando. Fla.
(8) Silver S. et al., 1988, Ann. Rev. Microbiol. 42:717-743
(9) U.S. Pat. No. 6,344,035—Chudzik, et al. Feb. 5, 2002
(10) U.S. Pat. No. 6,299,604—Ragheb, et al. Oct. 9, 2001
(11) U.S. Pat. No. 6,703,037—Hubbell et al. Mar. 9, 2004
(12) Valerio D. et al. Biomaterials, 19:1877-1884 (1998)
(13) U.S. Pat. No. 4,916,193—Tang et al. and U.S. Pat. No. 4,994,071—MacGrego
(13a) U.S. patent filed on Jun. 7, 2002, application Ser. No. 10/162,084, Santerre, Paul J.
(14) U.S. Pat. No. 5,798,115—Santerre, Paul J. and Mittleman, Marc W. Aug. 25, 1998.
(15) Modak S. M., Sampath, L., Fox, C. L., Benvenisty A., Nowygrod, R., Reemstmau, K. Surgery, Gynecology & Obstetrics, 164, 143-147 (1987).
(16) Bach, A.; Schmidt, H.; Bottiger, B.; Schreiber B.; Bohrer, H.; Motsch, J.; Martin, E.; Sonntag, H. G., *J. Antimicrob. Chemother.*, 37, 315, (1996)
(17) Nathan, A.; Zalipsky, S.; Ertel, S. I.; Agarthos, S. N.; Yarmush, M. L.; Kohn. J. *Bioconjugate Chem.* 1993, 4, 54-62.)
(18) Ghosh M. Progress in Biomedical polymers, Gebekin C G. Et al (ed), Plenum press, New York, 1990, 335-345; Ghosh M. Polymeric Materials, Science & Engineering 1988, 59: 790-793
(19) Coessens, V.; Schacht, E., Domurado, D. J. Controlled Release 1997, 47 283-291
(20) Roseeuw, E.; Coessens V.; Schacht E., Vrooman B.; Domurado, D.; Marchal G. J Mater. Sci: Mater. Med. 1999, 10, 743-746
(21) Hemmerich, K. J. *Polymer materials selection for radiation sterilized products*, Medical Device & Diagnostic Industry, February, 2000
(22) ISO 11137: Sterilization of health care products-Requirements for validation and routine control-Radiation sterilization.

SUMMARY OF THE INVENTION

Since the availability of drugs that can serve as commercial monomers, specifically designed for the synthesis of the above drug polymers or polymers to be used in composites are limited, there is a need for custom synthesis methods of the drug precursors. Rather than depending on the chemical function that common commercial drugs inherently provide, it would be better provide monomers that have similar multi-functional groups and preferably similar di-functional groups for the synthesis of hydrolysis or diol monomers that simultaneously incorporate the following features: 1) they are synthesized under mild conditions for coupling biological or pharmaceuticals or biocompatible components together via a hydrolysable bond; 2) they contain selectively reactive groups (di-functional or greater) (including amines (secondary or primary) and hydroxyls) that could be used for subsequent polymerization of polyesters, polyamides, polyurethanes, polysulfonamides and many other classical step growth polymers; 3) they contain selectively hydrolysable groups that permit the release of defined degradation products consisting of biological, pharmaceutical or biocompatible components; 4) their molecular weights may vary depending on the molecular weight of the pharmaceutical or biocompatible reagents to be as high as 4000, but typically the molecular weights of the molecules will be preferably less than 2000 in order for them to have good mobility of the molecular segment once incorporated within the polymer, and have good reactivity in the reaction polymerization solution; 5) they provide a strategy for enhancing the introduction of important biological, pharmaceutical or biocompatible reagents which otherwise contain functional groups (such as shielded esters, sulphonamides, amides and anhydrides) that would have poor reactivity in hydrolytic reactions due to strong van der Waals or hydrogen bonding between drug polymer backbones. 6) Since, these molecules will have similar functional groups they will provide consistent and more predictable reactivity in a classical step growth polymerization. This invention describes the unique synthesis pathways for the biomonomers, provides examples of their use in the synthesis of polymers and defines methods of processing said polymers for applications as biodegradable materials ranging from biomedical to environmental related products.

It is an object of the present invention to provide synthetic pathways of biological coupling agents/biomonomers comprising, such as, anti-inflammatory, anti-bacterial, anti-microbial and/or anti-fungal pharmaceuticals as biomonomer precursors with good reactivity for step growth polymer synthesis.

It is a further object of the present invention to provide biological polymers comprising said biological coupling compounds/monomers with pharmaceutically active properties.

It is a further object of the present invention to provide said polymer compounds alone or in admixture with a compatible polymeric biomaterial or polymer composite biomaterials for providing a shaped article having pharmaceutically active properties.

It is a further object of the present invention to provide said shaped article for use as a medical device, comprising a body fluid and tissue contacting device in the biomedical sector, or for use in the biotechnology sector to provide anti-infection, antiinflammatory properties.

it is a further object of the present invention to provide said polymer compounds alone as a coating or in admixture with either a base polyurethane, polysilicone, polyester, polyethersulfone, polycarbonate, polyolefin or polyamide for use as said medical devices in the biomedical sector, for improving anti-infection, anti-inflammatory, antimicrobials, anti-coagulation, anti-oxidation, anti-proliferation function.

It is a further object of the invention to provide processes of manufacture of said biomonomers, polymers containing said biomonomers, said admixtures and said shaped articles.

The invention, generally, provides the unique synthesis pathways for covalently coupling biologicals or pharmaceuticals or biocompatible components to both sides of a flexible diol or diamine, such as but not limited to triethylene glycol or any other kind of linear diol or diamine under mild conditions. Bioactive agents must possess a reactive group such as a carboxylic acid, sulfonate or phosphate group which can be conjugated to the flexible diols or diamines by using a carbodiimide-mediated reaction. Bioactive agents used in the coupling reaction must also contain selectively reactive multifunctional and preferably di-functional groups (including amines (secondary or primary) and hydroxyls) that could be used later on for subsequent polymerization of polyesters, polyamides, polyurethanes, polysulfonamides and any other classical step growth polymer pharmaceutic containing coupling agents/monomers.

The invention provides in one aspect, a biological coupling agent (biomonomer) having a central portion comprising of flexible i.e. not limiting chain dynamic movement such as do aromatic rings, linear or aliphatic (saturated) segments of <2000 theoretical molecular weight and hydrolysable linkages Accordingly, the invention provides a biological coupling agent of the general formula (III)

PBio-LINK A-PBio          (III)

wherein PBio is a biologically active agent fragment or precursor thereof linked to LINK A through a hydrolysable covalent bond and having at least one functional group to permit step growth polymerization; and LINK A is a coupled central flexible linear first segment of <2000 theoretical molecular weight linked to each of said PBio fragments.

By the term "biomonomers" in this specification and claims, is meant compounds of the formulae (III) used in the synthesis of the compounds of formula (I) through the use of the functional group for step growth polymerization.

Most preferably each of the PBio fragments is limited to a single functional group for use in step growth polymerization.

Thus, in a further aspect the invention provides a pharmaceutically-active polymeric compound of the general formula (1),

Y-[Y$_n$-LINK B-X]$_m$-LINK B          (I)

wherein (i) X is a coupled biological coupling agent of the general formula (II)

Bio-LINK A-Bio          (II)

wherein Bio is a biologically active agent fragment or precursor thereof linked to LINK A through a hydrolysable covalent bond; and LINK A is a coupled central flexible linear first segment of <2000 theoretical molecular weight linked to each of said Bio fragments;

(ii) Y is LINK B-OLIGO; wherein
  (a) LINK B is a coupled second segment linking one OLIGO to another OLIGO and an OLIGO to X or precursor thereof; and
  (b) OLIGO is a short length of polymer segment having a molecular weight of less than 5,000 and comprising less than 100 monomeric repeating units;
(iii) m is 1-40; and
(iv) n is selected from 2-50.

The invention provides in another aspect, a pharmaceutically-active polymeric material having a backbone made from said biomonomer. Such polymers comprise oligomeric segments of <5,000 theoretical molecular weight and optional link segments, herein denoted [link B] covalently coupled to the oligomeric segment denoted herein [oligo] and the said biomonomer.

By the term "oligomeric segment" is meant a relatively short length of a repeating unit or units, generally less than about 50 monomeric units and molecular weights less than 10,000 but preferably <5000. Preferably, [oligo] is selected from the group consisting of polyurethane, polyurea, polyamides, polyalkylene oxide, polycarbonate, polyester, polylactone, polysilicone, polyethersulfone, polyolefin, polyvinyl, polypeptide, polysaccharide; and ether and amine linked segments thereof.

By the term "LINK A molecule" is meant a molecule covalently coupling bioactive agents together in said biomonomer. Typically, LINK A molecules can have molecular weights ranging from 60 to 2000 and preferably between 60 to 700, and have multi-functionality but preferably di-functionality to permit coupling of two bioactive agents. Preferably the LINK A molecules are synthesized from the groups of precursor monomers selected from diols, diamines and/or compounds containing both amine and hydroxyl groups, with or without water solubility. Examples of typical LINK A precursors are given in Table 1 but they are not limited to this list.

TABLE 1

Ethylene glycol
Butane diol
Hexane diol
Hexamethylene diol
1,5 pentanediol
2,2-dimethyl-1,3 propanediol
1,4-cyclohexane diol
1,4-cyclohexanedimethanol -
Tri(ethylene glycol)
Poly(ethylene glycol), Mn: 100-2000
Polytethylene oxide) diamine, Mn: 100-2000
Lysine esters
Silicone diols and diamines
Polyether diols and diamines
Carbonate diols and diamines
Dihydroxy vinyl derivatives
Dihydroxy diphenylsulfone
Ethylene diamine
Hexamethylene diamine
1,2-diamino-2 methylpropane
3,3-diamino-N-methyldipropylamine
1,4 diaminobutane
1,7 diaminoheptane
1,8 diaminooctane By the term "LINK B molecule" is meant a molecule covalently coupling oligo units together to form the second coupling segments within the central portion. Typically, LINK B molecules can have molecular weights ranging from 60 to 2000 and preferably 60-700, and have difunctionality to permit coupling of two oligo units. Preferably the LINK B molecules are synthesized from diamines, diisocyanates, disulfonic acids, dicarboxylic acids, diacid chlorides and dialdehydes. Terminal hydroxyls, amines or carboxylic acids on the oligo molecules can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligoimines.

By the term "pharmaceutical or biologically active agent", or precursor thereof, is meant a molecule that can be coupled to LINK A segment via hydrolysable covalent bonding. The molecule must have some specific and intended pharmaceutical or biological action. Typically the [Bio] unit has a molecular weight ranging from 40 to 2000 for pharmaceuticals but may be higher for biopharmaceuticals depending on the structure of the molecule. Preferably, the Bio unit is selected from the group of anti-inflammatory, anti-oxidant, anti-coagulant, anti-microbial (including fluoroquinolones), cell receptor ligands and bio-adhesive molecules, specifically oligo-peptides and oligo-saccharides, oligonucleic acid sequences for DNA and gene sequence bonding, and phospholipid head groups to provide cell membrane mimics. The Bio component must have difunctional groups selected from hydroxyl, amine, carboxylic acid or sulfonic acid so that after coupling with Link A molecule, said biomonomer can react with the secondary groups of oligomeric segment to form LINK B linkage. The said secondary group may be protected during the reaction of primary groups with the LINK A.

TABLE 2

Typical Pharmaceutical Molecules Used For The Synthesis Of BiomonomerCoupling Agents

| Pharmaceuticals | Function | Chemical structures |
| --- | --- | --- |
| Norfloxacin | Antimicrobial | 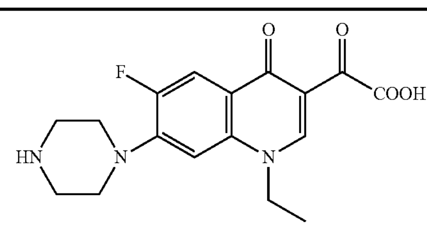 |

TABLE 2-continued

Typical Pharmaceutical Molecules Used For The Synthesis Of BiomonomerCoupling Agents

| Pharmaceuticals | Function | Chemical structures |
|---|---|---|
| Ciprofloxacin | Antimicrobial | 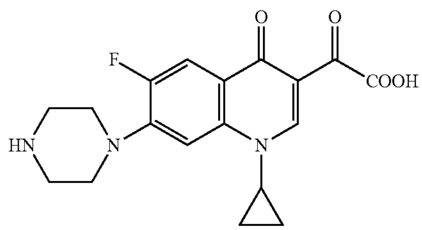 [SMILES: O=C(O)C(=O)c1cn(C2CC2)c2cc(N3CCNCC3)c(F)cc2c1=O] |
| Amfenac | Antiinflammatory | 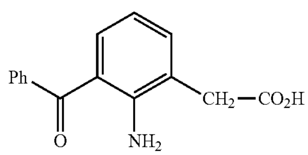 [SMILES: Nc1c(CC(=O)O)cccc1C(=O)c1ccccc1] |
| Aceclofenac | Antiinflammatory | 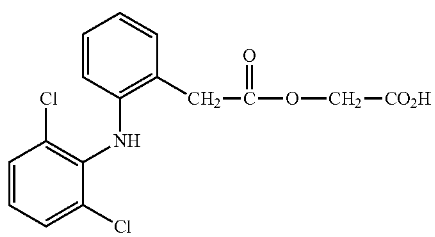 [SMILES: O=C(O)COC(=O)Cc1ccccc1Nc1c(Cl)cccc1Cl] |
| Oxaceprol | Antiinflammatory | 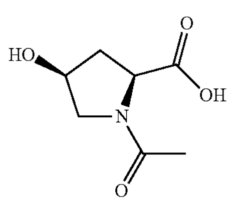 |
| Enoxolone | Antiinflammatory | 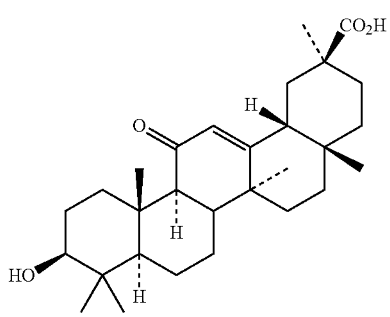 |
| Bromofenac | Antithrombic | 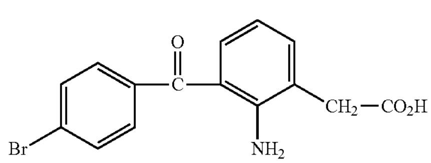 |
| Tirofiban | Antithrombic | 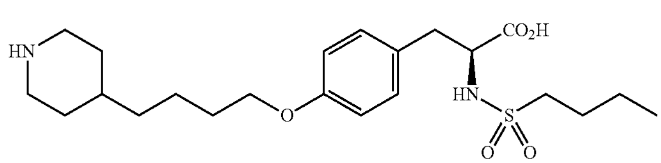 [SMILES: CCCCS(=O)(=O)N[C@@H](Cc1ccc(OCCCCC2CCNCC2)cc1)C(=O)O] |

TABLE 2-continued

Typical Pharmaceutical Molecules Used For The Synthesis Of BiomonomerCoupling Agents

| Pharmaceuticals | Function | Chemical structures |
|---|---|---|
| Tirofiban | Antithrombic | 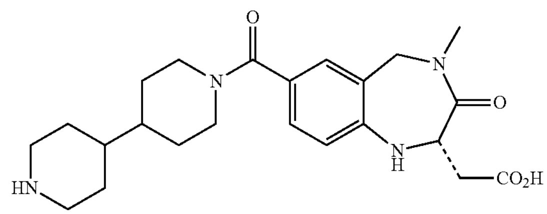 [SMILES: CN1Cc2cc(C(=O)N3CCC(C4CCNCC4)CC3)ccc2N[C@@H](CC(=O)O)C1=O] |
| Acivicin | Antiproliferation | 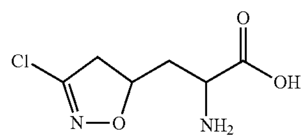 [SMILES: NC(CC1CC(Cl)=NO1)C(=O)O] |
| Alkeren | Antiproliferation | 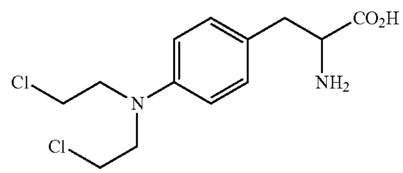 [SMILES: NC(Cc1ccc(N(CCCl)CCCl)cc1)C(=O)O] |

This invention is of particular value to those pharmacologically active compounds which are bioresponsive as hereinabove defined to provide in vivo a pharmacological active ingredient which has at least two functional groups but one of the functional groups has low reactivity with diisocyanates to form oligo-urethanes, or oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligo-imines. Such a pharmacological agent would include the fluoroquinolone family of antibiotics, or anticoagulants, anti-inflammatory or anti-proliferative agents of the type listed in Table 2 above.

The present invention is of particular use wherein the pharmacologically-active fragment is formed from the antibacterial 7-amino-1-cyclopropyl-4-oxo-1,4-dihydroquinoline and naphthyridine-3-carboxylic acids described in U.S. Pat. No. 4,670,444. The most preferred antibacterial members of these classes of compounds is 1-cyclopropyl-6-fluoro-1,4-dihydro-4-oxo-7-piperazine-quinoline-3-carboxylic acid and 1-ethyl-6-fluoro-1,4-dihydro-4-oxo-7-piperazine-quinoline-3-carboxylic acid having the generic name ciprofloxacin and norfloxacin, respectively. Others, of this class include sparfloxacin and trovafloxacin.

Without being bound by theory, it is believed that the presence of LINK A as herein defined, allows of a satisfactory "inter-bio distance" in the biologically-active polymer according to the invention, which inter-bio distance facilitates hydrolysis in vivo to release the biologically-active ingredient. LINK A offers a range of hydrolysis rates by reason of chain length variation and possibly, also, due to steric and conformational variations resulting from the variations in chain length.

Prior art compounds not having LINK A chain length variations but having LINK B chain lengths between the two biological entities cannot provide this advantageous variations in hydrolysis rates.

The present invention is of particular use wherein the pharmacologically active fragment is formed from the anti-inflammatory (2S,3S)-1-Acetyl-4-hydroxy-pyrrolidine-2-carboxylic acid having generic name Oxaceprol and (2S4aS,6aS,6bR,8aR,10S,12aS,12bR,14bR)-10-hydroxy-2,4a,6a,6b,9,9,12a-heptamethyl-13-oxo-1,2,3,4,4a,5,6,6a,6b,7,8,8a,9,10,11,12,12a,12b,13,14b-icosahydro-picene-2-carboxylic acid having the generic name Enoxolone.

The present invention is of particular use wherein the pharmacologically-active fragment is formed from the antithrombic (S)-2-(butane-1-sulfonylamino)-3-[4-(4-piperidin-4-yl-butoxy)phenyl]-propionic acid having the generic name Tirofiban and [(S)-7-([4,4']bipiperidinyl-1-carbonyl)-4-methyl-3-oxo-2,3,4,5-tetrahydro-1H-benzo[e][1,4]diazepin-2-yl]-acetic acid having the generic name Lotrafiban.

The present invention is of particular use wherein the pharmacologically-active fragment is formed from the anti-neuplastic (αS,5S)-α-amino-3-chloro-2-isoxazoleacetic-5-acetic acid having the generic name Acivicin and 4-[Bis(2-chloroethyl)amino-]-L-phenylalanine having the generic name Alkeren.

The oligomeric polymeric segment preferably has a molecular weight of <10,000; and more preferably, <5,000.

The term "theoretical molecular weight" in this specification is the term given to the absolute molecular weight that would result from the reaction of the reagents utilized to synthesize any given bioactive polymers. As is well known in the art, the actual measurement of the absolute molecular weight is complicated by physical limitations in the molecular weight analysis of polymers using gel permeation chromatography methods. Hence, a polystyrene equivalent molecular weight is reported for gel permeation chromatography measurements. Since many pharmaceutically active compounds absorb light in the UV region, the gel permeation chromatography technique also provides a method to detect the distribution of pharmaceutically active compound coupled within polymer chains.

The polymeric materials of use in the practice of the invention have polystyrene equivalent molecular weights of chains ranging from $2\times10^3$ to $1\times10^6$, and preferably in the range of $2\times10^3$ to $2\times10^5$.

In a further aspect, the invention provides compositions of polymers containing biomonomers alone or a base polymer in admixture with polymers containing biomonomers, as hereinabove defined, preferably in the form of a shaped article.

Examples of typical base polymers of use in admixture with aforesaid bioactive polymers according to the invention, includes polyurethanes, polysulfones, polycarbonates, polyesters, polyethylene, polypropylene, polystyrene, polysilicone, poly(acrylonitrile-butadienestyrene}, polyamide, polybutadiene, polyisoprene, polymethylmethacrylate, polyvinyl acetate, polyacrylonitrile, polyvinyl chloride, polyethylene terephtahate, cellulose and other polysacharides. Preferred polymers include polyamides, polyurethanes, polysilicones, polysulfones, polyolefins, polyesters, polyvinyl derivatives, polypeptide derivatives and polysaccharide derivatives. More preferably, in the case of biodegradable base polymers these would include segmented polyurethanes, polyesters, polycarbonates, polysaccharides or polyamides.

The polymers containing said biomonomers, or the admixed compositions according to the invention may be used as a surface covering for an article, or, most preferably, where the polymers or admixtures are of a type capable of being formed into 1) a self-supporting structural body, 2) a film; or 3) a fiber, preferably woven or knit. The composition may comprise a surface or in whole or in part of the article, preferably, a biomedical device or device of general biotechnological use. In the case of the former, the applications may include cardiac assist devices, tissue engineering polymeric scaffolds and related devices, cardiac replacement devices, cardiac septal patches, intra aortic balloons, percutaneous cardiac assist devices, extra-corporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, syringes, o-rings, bladders, penile implants, drug delivery systems, drainage tubes, pacemaker lead insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes. The applications of the latter include the synthesis of bioresorbable polymers used in products that are environmentally friendly (including but not limited to garbage bags, bottles, containers, storage bags and devices, products which could release reagents into the environment to control various biological systems including control of insects, biologically active pollutants, elimination of bacterial or viral agents, promoting health related factors including enhancing the nutritional value of drinking fluids and foods, or various ointments and creams that are applied to biological systems (including humans, animals and other).

In a preferred aspect, the invention provides an admixed composition, as hereinabove defined, comprising in admixture either a segmented polyurethane, a polyester, a polycarbonate, polysaccharide, polyamide or polysilicone with a compatible polymer containing said biomonomer.

The polymers containing said biomonomer, according to the invention, are synthesized in a manner that they contain a polymer segment, i.e. the [oligo] segments and said biomonomer in the backbone of polymer containing biochemical function with either inherent anti-coagulant, anti-inflammatory, anti-proliferation, anti-oxidant, antimicrobial potential, cell receptor ligands, e.g. peptide ligands and bio-adhesive molecules, e.g. oligosaccharides, oligonucleic acid sequences for DNA and gene sequence bonding, or a precursor of the bioactive component.

The in vivo pharmacological activity generated may be, for example, anti-inflammatory, anti-bacterial, anti-microbial, anti-proliferation, anti-fungal, but this invention is not limited to such biological activities.

BRIEF DESCRIPTION OF THE DRAWINGS

In order that the invention may be better understood, preferred embodiments will now be described by way of example only, with reference to the accompanying drawings wherein.

DETAILED DESCRIPTION OF PREFERRED EMBODIMENTS

Synthesis of Biomonomers

Figure 1:
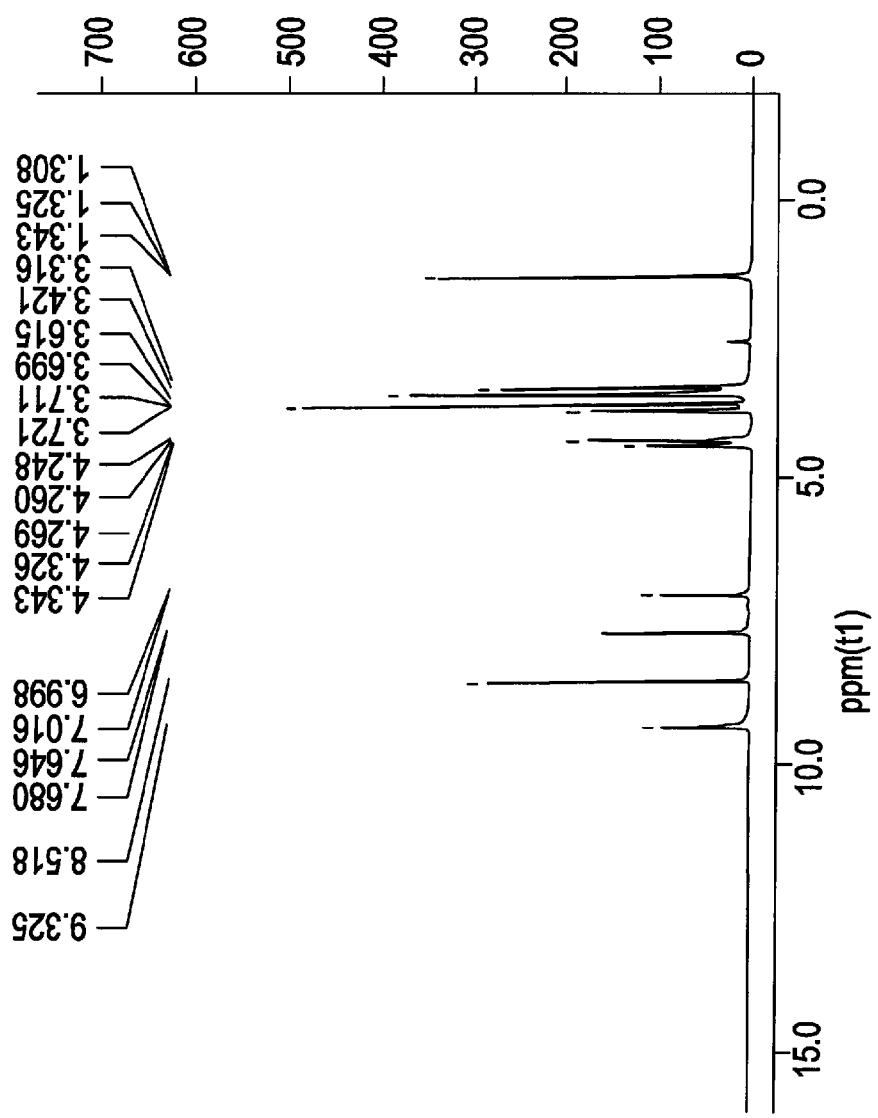
FIG. 1 is a proton nuclear magnetic resonance spectrum of biomononer NORF-TEG-NORF (norfloxacin-triethylene glycol-norfloxacin).

A description of the novel process for preparing the biological coupling agents/biomonomers of production D is set forth in Scheme A, where, R is CH₂CH₃ or cyclopropyl for norfloxacin and ciprofloxacin, respectively. Typically, linkA molecules have molecular weights ranging from 60 to 2000 and preferably 60 to 700, and must have at least di-functionality to permit coupling of at least two [Bio] units. The [Bio] unit has a molecular weight <2000 but may be higher depending on the structure of the molecule.

Preferred [Bio] components include but are not limited to the following categories and examples: Anti-inflammatory: non-steroidal-Oxaceprol, steroidal Enoxolone; antithrombotic: Tirofiban, Lotrafiban; anti-coagulant: heparin; anti-proliferation: acivicin and alkeren; anti-microbial: fluoroquinolones such as norfloxacin, ciprofloxacin, sparfloxacin and trovafloxacin and other fluoroquinolones.

Scheme A provides a general synthetic procedure for preparing the compounds of product D with formula (I).

Scheme 1: Synthetic route for bioactive monomers

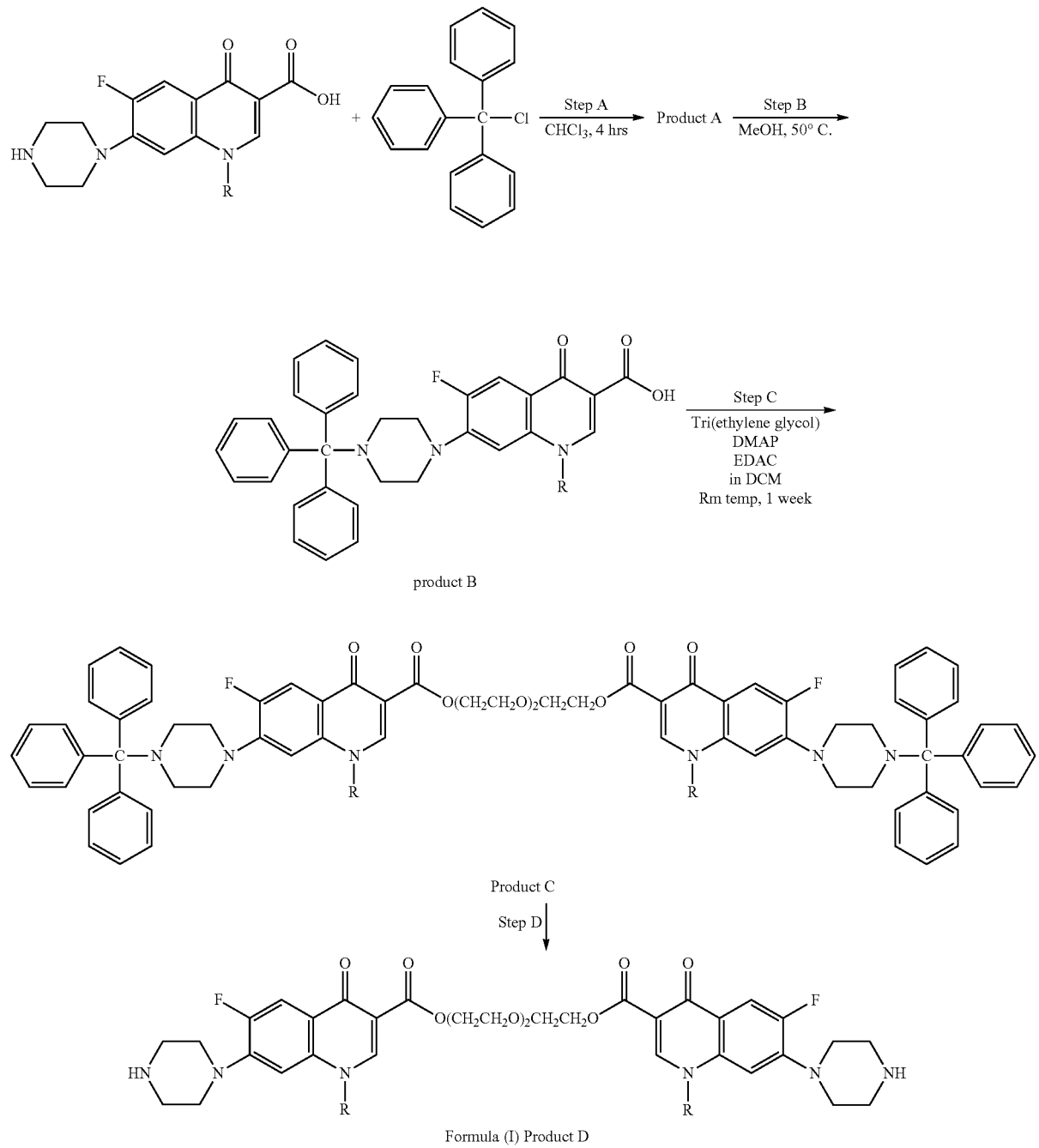

R: CH$_2$CH$_3$: Norfloxacin

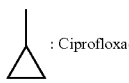 : Ciprofloxacin

DMAP: 4-(dimethylamino)pyridine
EDAC: 1-ethyl-3-(3-dimethylamino-propyl)carbodiimide
DCM: Dichloromethane In step A, a pharmaceutically active drug, such as norfloxacin or ciprofloxacin (in the form of hydrochloride salt) is reacted with protecting groups such as trityl halides in the presence of triethylene amine to provide an intermediate with both amine and carboxylic acid groups protected with a trityl group. It is understood by those skilled in the art that other protecting groups can be used as exemplified in this document's examples.

A suitable trityl halide is reacted with norfloxacin or ciprofloxacin hydrochloride salt in a suitable solvent, such as chloroform. Many other solvents may be needed depending on the solubility of the selected protecting groups and the agents forming the biomonomer. Suitable trityl halides include trityl chloride and trityl bromide. A preferred trityl halide is trityl chloride. The amount of trityl halide ranges from 2 to. 4 molar equivalent of norfloxacin/ciprofloxacin, a preferred amount is 2.2 molar equivalents. Triethylamine is added to scavenge free HCl which is generated as a byproduct. A little excess amount of triethylamine will avoid the deprotection of the N-triethylamine group in the following selective hydrolyzation step. In the case of ciprofloxacin, an excess molar amount of triethylene amine such as 2 to 4 times was added into reaction mixture. A preferred amount is 3 times. The reaction mixture is stirred for a period of time ranging from 2-24 hours in a temperature range of 0° C. to 60° C. A preferred stirring time is 4 hours and a preferred temperature is 25° C. A homogenous solution is obtained. Following this step, product A is left in the reaction solution for the next step of the in-situ reaction. No isolation of the product A is required during processing.

In step B, the reaction product of step A, such as norfloxacin/ciprofloxacin with both amine and carboxylic acid groups protected with trityl group, is selectively deprotected to yield product B containing free carboxylic acid and N-triethylamine groups.

For example, in step B, a large amount of methanol was added into the reaction mixture of step A. The volume of methanol ranges from equivalent to two times that of the solvent used in step A. A preferred volume is 1.5 times that of the solvent volume.

The reaction mixture is stirred for 1-24 hrs in a temperature range from 25° C. to 60° C. A preferred stirring time is 2 hrs and a preferred temperature is 50° C. The selectively deprotected fluoroquinolone material is precipitated from the reaction solution. Product B is recovered from the reaction zone by filtration after the reaction mixture is cooled down to room temperature. Product B is further purified from CHCl$_3$/methanol by standard recrystallization method.

In step C, the purified amine-protected fluoroquinolone is coupled to both sides of a diol or diamine (in this example, triethylene glycol is used) containing a flexible and/or water-soluble central portion.

For example, the purified amine-protected fluoroquinolone (Product B) is coupled to a tri(ethylene glycol) in the presence of a suitable coupling agent such as 1-ethyl-3-(3-dimethylamino-propyl)carbodiimide herein denoted as EDAC and an appropriate base such as 4-(dimethylamino)pyridine herein denoted as DMAP as a catalyst. Other coupling reagents may include various carbodiimides such as CMC (1-cyclohexyl-3-(2-morpholinoethyl)carbodiimide), DCC(N,N'-dicyclohexyl-carbodiimide), DIC (Diisopropyl carbodiimide) etc, but are not limited to these. The amount of diol ranges from 0.3 to 0.5 molar equivalent of product B. A preferred amount of dial is 0.475 molar equivalent of product B. The amount of coupling agent EDAC ranges from 2 to 10 times molar equivalent of product B. A preferred amount of EDAC is 8 times molar equivalent. The amount of base DMAP can range from 0.1 to equal molar amount of product B. A preferred amount is 0.5 molar equivalents. The reaction was carried out in a suitable solvent such as dichloromethane under a noble atmosphere such as nitrogen, argon. Other solvents may be appropriate depending on their solubility properties with product B and their potential reactivity with the reagents. The reactants are typically stirred together for a period of time ranging from 24 hours to 2 weeks at a temperature range from 0° C. to 50° C. A preferred stirring time is one week and a preferred temperature is 25° C.

After the reaction is finished, solvent is removed by rotary evaporator. The residues are washed with water several times to remove soluble reagents such as EDAC. The solids are then dissolved in chloroform. Product C in Scheme 1 is recovered from the solution by standard extractive methods using chloroform as the extraction solvent. Product C was isolated by column chromatography using a developer made up of chloroform/methanol/ammonia hydroxide aqueous solution (9.2:0.6:0.2). Product C is further purified with recrystallization techniques from chloroform and methanol.

In step D, the N-trietylamine groups of the purified product C are deprotected to yield the corresponding desired pharmaceutical coupling agent/biomonomer.

For example, the appropriate product C is reacted with a small amount of water in the presence of a small amount of weak acid, such as trifluoroacetic acid, in a suitable organic solvent such as dichloromethane. The amount of water can range from 1% to 10% volume percentage and a preferred amount is 1%. The amount of trifluoroacetic acid is between 1% to 10% volume percent, with a preferred amount being 2%. The reaction mixture is stirred within a temperature range of 0° C. to 50° C. over a time period of 2 to 24 hours. A preferred temperature is 25° C. and a preferred time period is 4 hours. Product D is precipitated from reaction solution and collected by filtration. The product is further purified by washing with CHCl$_3$.

Use of Biomonomers in a Polymer Synthesis.

The pharmaceutically active polymers are synthesized in a traditional stepwise polymerization manner as are well known in the art. A multi-functional LINK B molecule and a multi-functional oligo molecule are reacted to form a prepolymer. The prepolymer chain is extended with said biomonomer to yield a polymer containing the biomonomers. Non-biological extenders such as an ethylene diamine, butane diol, ethylene glycol and others may also be used. The linkB molecule is preferably, but not so limited, to be di-functional in nature, in order to favour the formation of a linear polymer containing biomonomers. Preferred linkB molecules for biomedical and biotechnology applications are diisocyanates: for example, 2,4 toluene diisocyanate; 2,6 toluene diisocyanate; methylene bis(p-phenyl)diisocyanate; lysine diisocyanato esters; 1,6 hexane diisocyanate; 1,12 dodecane diisocyanate; bis-methylene die cyclohexyl isocyanate); trimethyl-1,6 diisocyanatohexane, dicarboxylic acids, di-acid chlorides, disulfonyl chlorides or others. The oligo component is preferably, but not so limited, difunctional, in order to favor the formation of a linear polymer containing said biomonomers. Preferred oligo components are terminal diamine and diol reagents of: for example, polycarbonate, polysiloxanes, polydimethylsiloxanes; polyethylene-butylene co-polymers; polybutadienes; polyesters including polycaprolactones, polylactic acid, and other polyesters; polyurethane/sulfone co-polymer; polyurethanes; polyamides; including oligopeptides (polyalanine, polyglycine or copolymers of amino-acids) and polyureas; polyalkylene oxides and specifically polypropylene oxide, polyethylene oxide and polytetramethylene oxide. The molecular weights of the [oligo] groups are less than 10,000, but preferably have molecular weights of less than 5000. Synthesis of the prepolymers to the bioactive polymer can be carried out by classical urethane/urea reactions using the desired combination of reagents but with the excess amount of linkB molecules in order to end-cap the prepolymer with linkB molecule. When the prepolymer with desired chain length is reached, said biomonomer is added to extend the prepolymer chain giving a final bioactive polymer. Alternatively the biomonomers may be substituted for inclusion as the oligo groups.

Bioactive polymers can be synthesized with different components and stoichiometry. Prior to synthesis, the LINK B molecules are, preferably, vacuum distilled to remove residual moisture. The biomonomers are desiccated to remove all moisture. Oligo components are degassed overnight to remove residual moisture and low molecular weight organics.

While reactants can be reacted in the absence of solvents if practical, it is preferable to use organic solvents compatible with the chemical nature of the reagents, in order to have good control over the characteristics of the final product. Typical organic solvents include, for example, dimethylacetamide, acetone, tetrahydrofuran, ether, chloroform, dimethylsulfoxide and dimethylformamide. A preferred reaction solvent is dimethylsulfoxide (DMSO, Aldrich Chemical Company, Milwaukee, Wis.).

In view of the low reaction activity of some diisocyanates, e.g. DDI and THDI, with oligo precursor diols, a catalyst is preferred for the Synthesis. Typical catalysts are similar to those used in the synthesis of urethane chemistry and, include, dibutyltin dilaurate, stannous octoate, N,N' diethylcyclohexylamine, N-methylmorpholine, 1,4 diazo (2,2,2) bicyclo-octane and zirconium complexes such as Zr tetrakis (2,4-pentanedionato) complex.

In the first step of the preparation of a prepolymer, for example, the linkB molecules are added to the oligo component and, optionally, catalyst to provide the prepolymer of the bioactive polymer. The reaction mixture is stirred at a temperature of 60° C. for a suitable time period, which depends on the reaction components and the stoichiometry. Alternate temperatures can range between 25° C. to 110° C. Subsequently, said biomonomer is added to the prepolymer and, generally, the mixture is allowed to react overnight. The reaction is terminated with methanol and the product is precipitated in ether or a mixture of distilled water with ether or other suitable solvents. The precipitate is dissolved in a suitable solvent, such as acetone and precipitated in ether or a mixture of distilled water with ether again. This process was repeated 3 times in order to remove any residual catalyst compound. Following washing, the product is dried under vacuum at 40° C.

Alternatively, the biomonomers can be used to make polyamides using classical reactions such as those described below.

Fabrication of Product:

The pharmaceutical polymers containing biomonomers are either used alone or admixed with suitable amounts of base polymers in the fabrication of article products. If admixed in a blend, then suitable polymers may include polyurethane, polyester or other base polymers. Product may be formed by; 1) compounding methods for subsequent extrusion or injection molding or articles; 2) co-dissolving of base polymer with bioactive polymer into a solvent of common compatibility for subsequent casting of an article in a mold or for spinning fibers to fabricate an article; 3) wetting the surface of an article with a solution of bioactive polymer or a blend in solvent of common compatibility with a polyurethane or other polymer to which the bioactive polymer solution is being applied; or 4) in admixture with a curable polyurethane, for example, 2 part curing system such as a veneer. All of the above processes can be used with the pure polymer, containing the biomonomer groups or with blends of said polymer and common biomedical polymers.

The invention, thus, provides the ability to synthesize a range of novel polymeric materials possessing intramolecular properties of pharmaceutical or biological nature. When said polymers are used alone or in admixture with, for example, a polyurethane, the bioactive polymer provides the composite having better pharmaceutical function, particularly for use in medical devices, promoting cell function and regulation, tissue integration, pro-active blood compatibility and specifically anti-coagulant/platelet function, biostability function, anti-microbial function and anti-inflammatory function, or for use in the biotechnology sector for biological activity.

The application for these materials include the synthesis of bioresorbable polymers used in medical device products that require the delivery of biologicals, pharmaceuticals or the release of biocompatible materials upon biodegradation within or in contact with a biological body (human or animal). This includes the manufacturing of products in the form of films (cast or heat formed), fibres (solvent or melt spun), formed into composite materials (polymers combined in any form with ceramics, metals or other polymers) of any shape, injection molded, compression molded, extruded products. Such product can include but are not limited to: cardiac assist devices, tissue engineering polymeric scaffolds and related devices, cardiac replacement devices, cardiac septal patches, intra aortic balloons, percutaneous cardiac assist devices, extra-corporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, syringes, o-rings, bladders, penile implants, drug delivery systems, drainage tubes, pacemaker lead insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes.

Other non-medical applications may include of bioresorbable polymers used in products that are environmentally friendly (including but not limited to garbage bags, bottles, containers, storage bags and devices, products which could release reagents into the environment to control various biological systems including control of insects, biologically active pollutants, elimination of bacterial or viral agents, promoting health related factors including enhancing the nutritional value of drinking fluids and foods, or various ointments and creams that are applied to biological systems (including humans, animals and other).

In these examples, the following acronyms are used.

NORF (Norfloxacin)
CIPRO (Ciprofloxacin)
OC (Oxaceprol)
POC (Protected Oxaceprol)
TF (Tirofiban)
PTF (Protected Tirofiban)
AK (Alkeren)
PAK (Protected Alkeren)
AF (Amfenac)
AV (Acivicin)
BF (Bromfenac)
TEG (Triethylene glycol)
HDL (1,6-Hexanediol)
HDA (1,6-Hexanediamine)
TrCl (Trityl Chloride)
DMAP (4-(dimethylamino)pyridine)
EDAC (1-ethyl-3-(3-dimethylamino-propyl)carbodiimide)
TEA (Triethylene amine)
TFA (Trifluoroacetic acid)
THDI (trimethyl-1,6 diisocyanatohexane)
PCL polycarprolactone diol
AC (Adipoyl Chloride)
THDI/PCL/TEG (segmented polyurethane)
DBTL (dibutyltin dilaurate)
DCM (Dichloromethane)
DMF (dimethylformamide)
TLC (thin layer chromatography)
CC (Column chromatography)

Where appropriate all isocyanate reactions were catalysed with DBTL (dibutyltin dilaurate).

Nuclear magnetic resonance was used to identify the structure of the biomonomer.

Mass spectroscopy was used to confirm the molar mass of the synthesized biomonomer.

Gel permeation chromatography was used to define the distribution of [Bio] the moiety within the drug polymer and to estimate relative molecular weights of the polymer.

Characterization of tin residues located at the surface of the drug polymer coatings was demonstrated using X-ray photoelectron spectroscopy (measuring chemical composition) at 90 degree. Elimination of tin residues is important for biological applications since the latter is toxic.

In vitro evaluation of antimicrobial release and biodegradation were performed in order to assess the rates of degradation for the different antimicrobial polymer formulations and determines periods of efficacy. In these studies the polymers are incubated with enzytne and the solution is recovered for separation of degradation products. Hydrolytic enzymes related to monocyte macrophages, specifically cholesterol esterase, and neutrophils (elastase), with in a pH 7 phosphate buffered saline solution may be used for in vitro tests over a 10-week time frame. Degradation products may be characterized using High Performance Liquid Chromatography (HPLC), combined with mass spectroscopy.

Minimum inhibitory concentration (MIC) assays were used to evaluate the antimicrobial activity of incubating solutions obtained from drug polymer biodegradation studies against *P. aeruginosa*. Turbidity of each culture was recorded to evaluate the inhibitory properties of degradation solution of drug polymers.

Sterilization stability of drug polymers was estimated after drug polymers were sterilized by γ-radiation sterilization (radiation dose: 25 Kgy), a standard method in the medical device field. GPC measurements were carried on with these samples before and after they were radiated and after a time period of 1 to 4 weeks.

Biocompatibility study of the drug polymers was also performed in order to assess the biocompatibility of control and drug polymers with mammalian cells. In this study, HeLa cells were cultured directly onto the polyurethane polymers films and incubated at 37° C. for 24 hours. Cell viability was measured by staining for succinate dehydrogenase.

In vivo animal studies are performed on substrates, devices or articles according to the invention formed in whole or in part of bioactive polymers. The articles containing either bioactive polymer or non-bioactive control polymer were implanted in the peritonitis of male rats accompanied with an inoculation of *P. aeruginosa* bacteria. The articles were explanted after rats were housed for 1 week. The effect of the antimicrobial polymer was evaluated.

EXAMPLES

The following examples illustrate the preparation of biomonomers and bioresponsive pharmacologically active polymers according to the invention.

Example 1

NORF-TEG-NORF and CIPRO-TEG-CIPRO are examples of antimicrobial drug containing biomonomers according to the invention. The example shows the use of a single drug or combination of drugs. The conditions of synthesis for this reaction are as follows.

In step A, of NORF (1.3 g, 4 mmol)/or CIPRO hydrochloride salt (4 mmol) were reacted with trityl chloride (2.7 g, 8.8 mmol) and TEA (0.6 ml, 8 mmol) (Aldrich, 99%)/or 12 mmol of TEA in the case of CIPRO in 40 ml of $CHCl_3$ for four hours at room temperature. A clear solution was obtained.

In step B, 40 ml of methanol was added into the above clear solution. The mixture was heated to 50° C. and stirred for one hour; a precipitate appeared in the solution. After the reaction mixture was cooled down to room temperature, precipitates were collected by filtration. The precipitate was further purified from $CHCl_3$/methanol. 3.4 mmol of Product B were obtained. Yield was usually greater than 85%.

In step C, Product B (20 mmol), TEG (1.44 g, 9.5 mmol), DMAP (1.24 g, 10 mmol) were dissolved in 100 ml DCM. EDAC (31 g, 160 mmol) was then added into the reaction system. The reaction mixture was stirred at room temperature under a nitrogen atmosphere for one week. After reaction was finished, DCM was removed by rotary evaporator. The residues were washed with de-ionized water several times to remove soluble reagents such as the by-product of urea. The solids were then dissolved in chloroform and washed with de-ionized water again. The crude product of the reaction was recovered from the solution by extraction. Product C was isolated by column chromatograph using the developer of chloroform/methanol/ammonia hydroxide aqueous solution (9.2:0.6:0.2). Product C is further purified with recrystallization technique from chloroform and methanol. Product C can be obtained with a yield of 85%.

In step D, the purified product C (5.4 g, 4.4 mmol) was dissolved in chloroform containing one volume percent of water and 1 volume percent of trifluoroacetic acid. The reaction solution was stirred at room temperature for 4 hrs. White precipitates that were produced in the reaction were collected by filtration and purified by washing with chloroform. Following washing Product D, i.e. the biomonomer was dried in vacuum oven for 24 hours at a temperature of 40° C. The pure Product D i.e. said biomonomer can be obtained with a yield of 95%.

$^1$H NMR of NORF-TEG-NORF: (400 MHz, DMSO). δ: 9.33 (bs, 2H, NH), 8.52 (s, 2H, H$^2$, ar), 7.66 (d, 2H, J=13.6 Hz, H$^5$, ar), 7.01 (d, 2H, J=7.2 Hz, H$^8$, ar), 4.33 (q, 4H, J=6.8 Hz, N—CH$_2$—CH$_3$), 4.26 (t, 4H, J=4.8 Hz, CO$_2$CH$_2$), 3.71 (t, 4H, J=4.8 Hz, CO$_2$CH$_2$CH$_2$) 3.48-3.28 (m, 16 A, piperazine), 1.33 (t, 6H, J=6.8 Hz, NCH$_2$CH$_3$). [FIG. 1]

Figure 2:
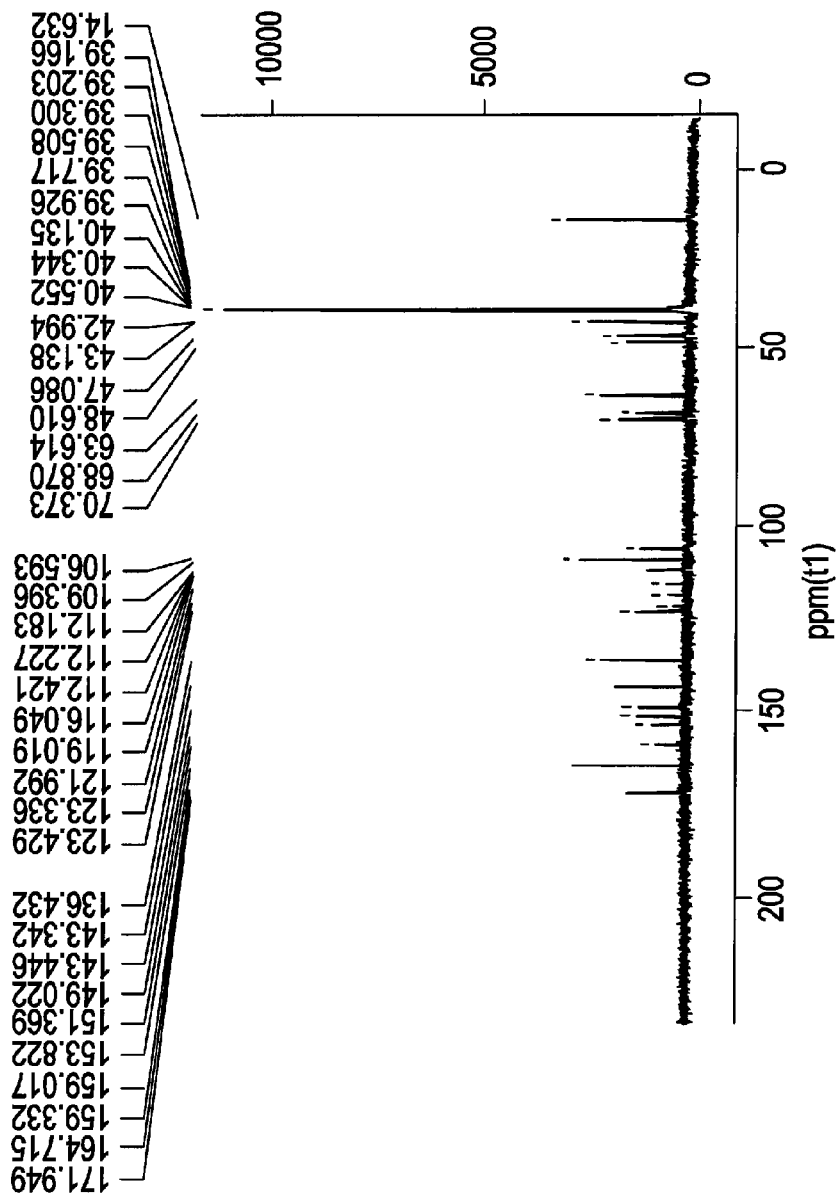
FIG. 2 is the carbon nuclear magnetic resonance spectrum of biomonomer NOF-TEG-NORF.

$^{13}$C NMR of NORF-TEG-NORF: (400 MHz, DMSO). δ: 171.9, 164.7, 159.3, 159.0, 153.8, 151.4, 149.0, 143.4, 143.3, 136.4, 123.4, 122.0, 119.0, 116.0, 112.4, 109.4, 106.6, 70.4, 68.9, 63.6, 48.6, 47.1, 43.1, 43.0, 14.6, [FIG. 2]

Figure 3:
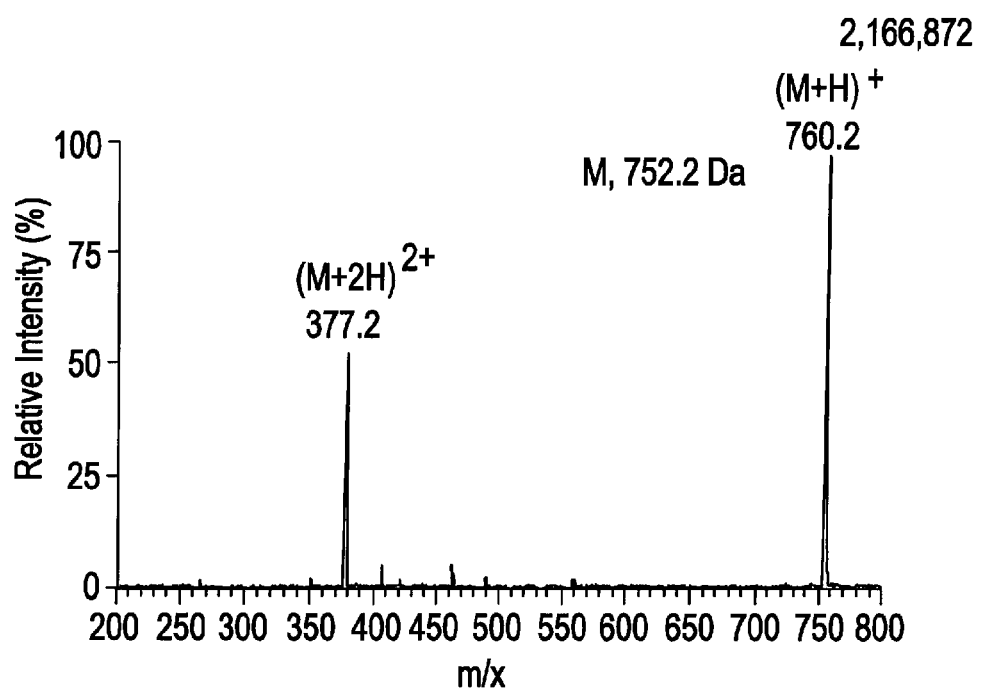
FIG. 3 is a positive electrospray mass spectrum of biomonomer NORF-TEG-NORF.

ES-MS of NORF-TEG-NORF (m/z, %) (Positive mode): Calculated for mass C$_{38}$H$_{46}$F$_2$N$_6$O$_8$: 752 amu. found 753, 377 (M+2H)$^+$. [FIG. 3]

Figure 4:
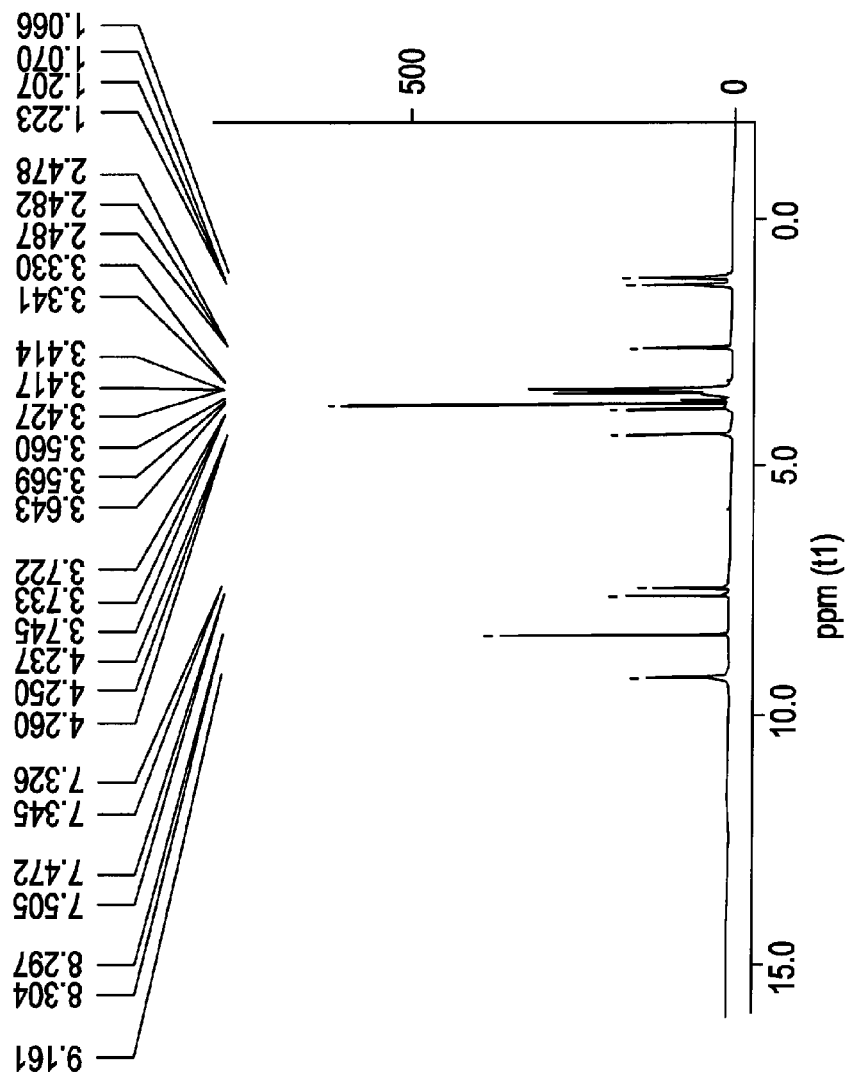
FIG. 4 is a proton nuclear magnetic resonance spectrum of biomononer CIPRO-TEG-CIPRO (ciprofloxacin-triethylene glycol-ciprofloxacin).

$^1$H NMR of CIPRO-TEG-CIPRO: (400 MHz, DMSO). δ: 9.16 (bs, 2H, NH—R), 8.30 (s, 2H, H$^2$, ar), 7.49 (d, 2H, J=13.2 Hz, H$^5$, ar), 7.34 (d, 2H, J=7.6 Hz, H$^8$, ar), 4.25 (t, 4H, J=5.2 Hz, N—CH(CH$_2$)$_2$); 3.73 (t, 4H, J=4.4 Hz, CO$_2$CH$_2$), 3.46-3.30 (m, 16H, piperazine), 1.22 (q, 4H, J=6.4 Hz, CH(CH$_2$CH$_2$)), 1.07 (m, 4H, CH(CH$_2$CH$_2$)). [FIG. 4]

$^{13}$C NMR of CIPRO-TEG-CIPRO: (400 MHz, DMSO). δ: 171.9, 164.1, 158.7, 153.9, 151.5, 148.4, 143.0, 142.9, 138.1, 122.6, 122.5, 111.9, 111.7, 109.2, 107.0, 79.6, 70.5, 70.4, 68.9, 63.7, 47.0, 43.2, 35.3, 7.9. [FIG. 5]

Figure 6:
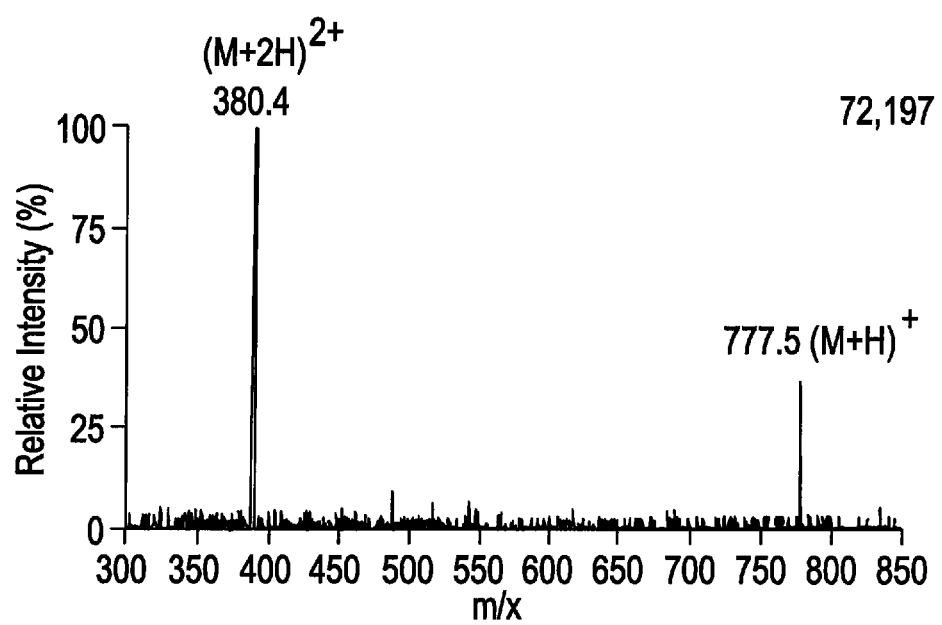
FIG. 6 is a positive electrospray mass spectrum of biomonomer CIPRO-TEG-CIPRO.

ES-MS of CIPRO-TEG-CIPRO (m z, %) (Positive mode): Calculated for mass C$_{40}$H$_{46}$F$_2$N$_6$O$_8$: 776 amu. found 777 (M+H$^+$); 389 (M+2H)$^+$. [FIG. 6]

Example 2

CIPRO-HDL-CIPRO is example of biomonomer according to the invention and different from example 1 by the introduction of a hydrophobic link A molecule rather than hydrophilic link A molecule. The conditions of synthesis for this reaction are as follows.

The reaction conditions for selectively protecting amine groups of CIPRO are the same as the step A and B in Example 1.

In step C, Product B (20 mmol), HDL (9.5 mmol), DMAP (1.24 g, 10 mmol) were dissolved in 100 ml DCM. EDAC (31 g, 160 mmol) was then added into reaction system. The reaction mixture was stirred at room temperature under a nitrogen atmosphere for one week. After the reaction was finished, DCM was removed by rotary evaporator. The residues were washed with de-ionized water several times to remove soluble reagents such as the by-product of urea. The solids were then dissolved in chloroform and washed with de-ionized water again. The crude product of the reaction was recovered from the solution by extraction. Product C was isolated by column chromatography using the developer of chloroform/methanol/ammonia hydroxide aqueous solution (9.2:0.6:0.2). Product C is further purified with a recrystallization technique from chloroform and methanol.

In step D, the purified product C (4 mmol) was dissolved in chloroform containing one volume percent of water and 1 volume percent of trifluoroacetic acid. The reaction solution was stirred at room temperature for 4 hrs. White precipitates produced in the reaction were collected by filtration and purified by washing with chloroform. Following washing Product D, i.e. the biomonomer was dried in vacuum oven for 24 hours at a temperature of 40° C.

Example 3

NORF-HDA-NORF is example of biomonomer according to the invention and different from example 1 in that a diamine is used to generate an amide rather than ester linkage in the biomonomer. The conditions of synthesis for this reaction are as follows.

The reaction conditions for selectively protecting amine groups of NORF are the same as the step A and B in Example 1.

In step C, Product B (20 mmol), HDA (9.5 mmol), DMAP (1.24 g, 10 mmol) were dissolved in 100 ml DCM. EDAC (31 g, 160 mmol) was then added into reaction system. The reaction mixture was stirred at room temperature under a nitrogen atmosphere for one week. After the reaction was finished, DCM was removed by rotary evaporator. The residues were washed with de-ionized water several times to remove soluble reagents such as the by-product of urea. The solids were then dissolved in chloroform and washed with de-ionized water again. The crude product of the reaction was recovered from the solution by extraction. Product C was isolated by column chromatography using the developer of chloroform/methanol/ammonia hydroxyl aqueous solution (9.2:0.6:0.2). Product C is further purified with recrystallization technique from chloroform and methanol.

In step D, the purified product C (4 mmol) was dissolved in chloroform containing one volume percent of water and 1 volume percent of trifluoroacetic acid. The reaction solution was stirred at room temperature for 4 hrs. White precipitates produced in the reaction were collected by filtration and purified by washing with chloroform. Following washing Product D, i.e. the biomonomer was dried in vacuum oven for 24 hours at a temperature of 40° C.

Example 4

OC-TEG-OC is an example of anti-inflammatory drug containing biomonomer according to the invention. The biomonomer was synthesized using Oxaceprol (OC), by reacting the carboxylic acid with the hydroxyl of TEG and leaving the hydroxyl for subsequent use in the polymerization. The conditions of synthesis for this reaction are as follows.

In step A, OC (11.55 mmol) was reacted with t-butyldimethylsilyl chloride (28.87 mmol) and 1,8-diazabicylco[5.4.0]undec-7-ene (30.03 mmol) in 4 ml of acetonitrile at 0° C. during the addition of the base and then overnight at ambient temperature. A precipitate developed during the progress of the reaction The precipitate was filtered.

In step B, the filtrate was treated with water (10 ml) and extracted with n-pentane (2×5 ml). The solvent for the aqueous portion was removed under reduced atmosphere. The residue was dissolved in methanol (10 mL), tetrahydrofuran (5 mL), water (5 mL) and then treated with 2N aqueous sodium hydroxide (8 mL). The reaction mixture was stirred for 1.5 h at room temperature, adjusted to a pH=3 with 1 N HCl, concentrated and filtered. The precipitate obtained was recrystallized from water and afforded pure 4 (2.79 g, 84%).

$^1$H NMR: (400 MHz, CDCl$_3$) δ: 4.87 (bs, 1H, CO$_2$H), 4.61 (dd, 1H, J=8.0 Hz, 6.4 Hz, CHCO$_2$H), 4.48 (p, 1H, J=4.4 Hz, CHOSi), 3.67 (dd, 1H, J=10.4 Hz, 4.8 Hz, CHHN), 3.36 (dd, 1H, J=10.4 Hz, 6.0 Hz, CHHN), 2.36 (dt, 2H, J=13.2 Hz, 5.2

Figure 7:
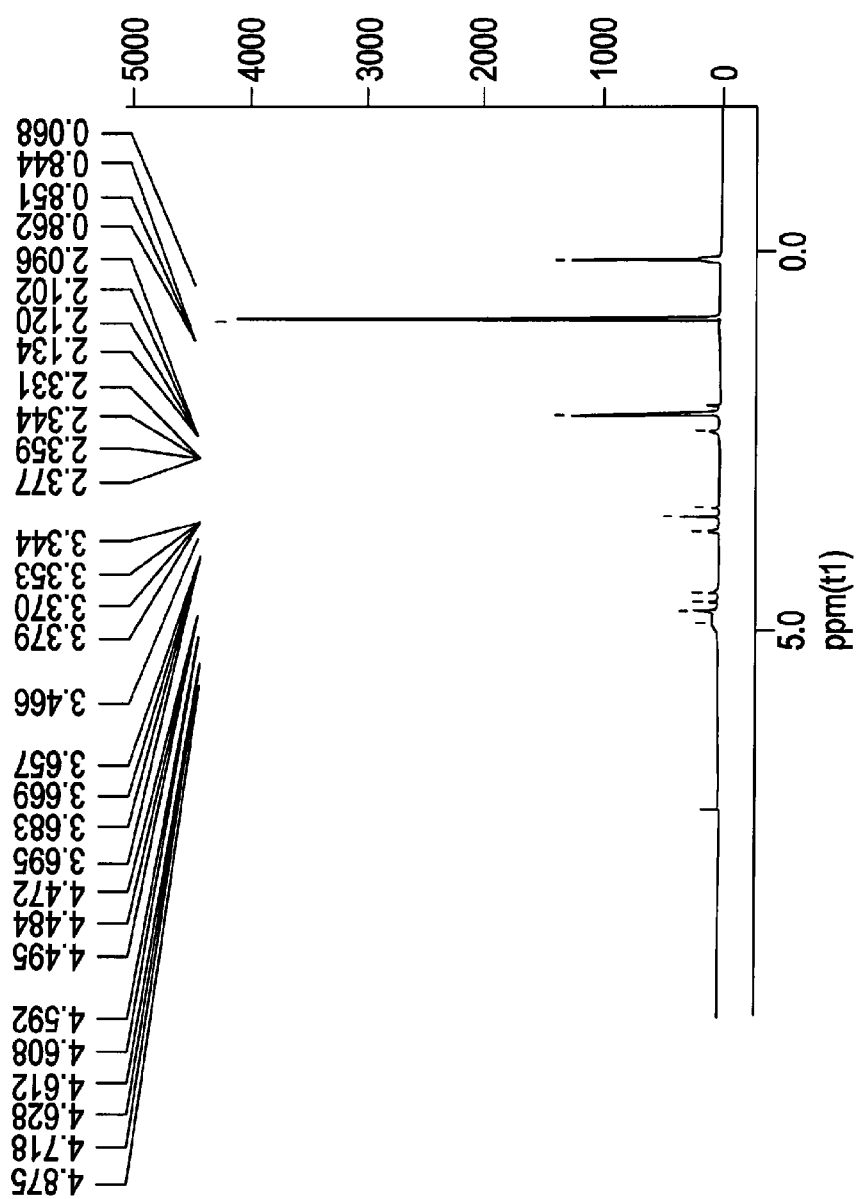
FIG. 7 is a proton nuclear magnetic resonance spectrum of POC (protected oxaceprol).

Hz, 2H, CH$_2$CHCO$_2$H), 2.12 (s, 3H, COCH$_3$), 0.86 (s, 9H, C(CH$_3$)$_3$), 0.08 (s, 3H, SiCH$_3$), 0.07 (s, 3H, SiCH$_3$). [FIG. 7]

$^{13}$C NMR: (400 MHz, CDCl$_3$) δ: 172.7, 172.3, 70.0, 58.3, 56.2, 37.1, 25.6, 22.2, 17.9, −4.8, −5.0. [FIG. 8]

ES-MS (m/z, %) (Negative mode): Calculated for mass C$_{13}$H$_{25}$NO$_4$Si: 287 amu. found 286.1. [FIG. 9]

In step C, Product B (3.48 mmol), TEG (1.58 mmol), DMAP (0.16 mmol) were dissolved in DCM (5 ml). EDAC (3.95 mmol) was then added into the reaction solution cooled to 0° C. The resulting solution was stirred for 1 h at 0° C., the cooling was removed, and the mixture was stirred for 5 days at ambient temperature. The solvent was removed under reduced pressure. Water (20 mL) and the system was extracted with pentane (3×10 mL). The combined pentane extracts where dried using sodium sulphate, filtered, and the solvent removed under reduced pressure. This produced 0.74 g (67%) of the desired product.

Figure 10:
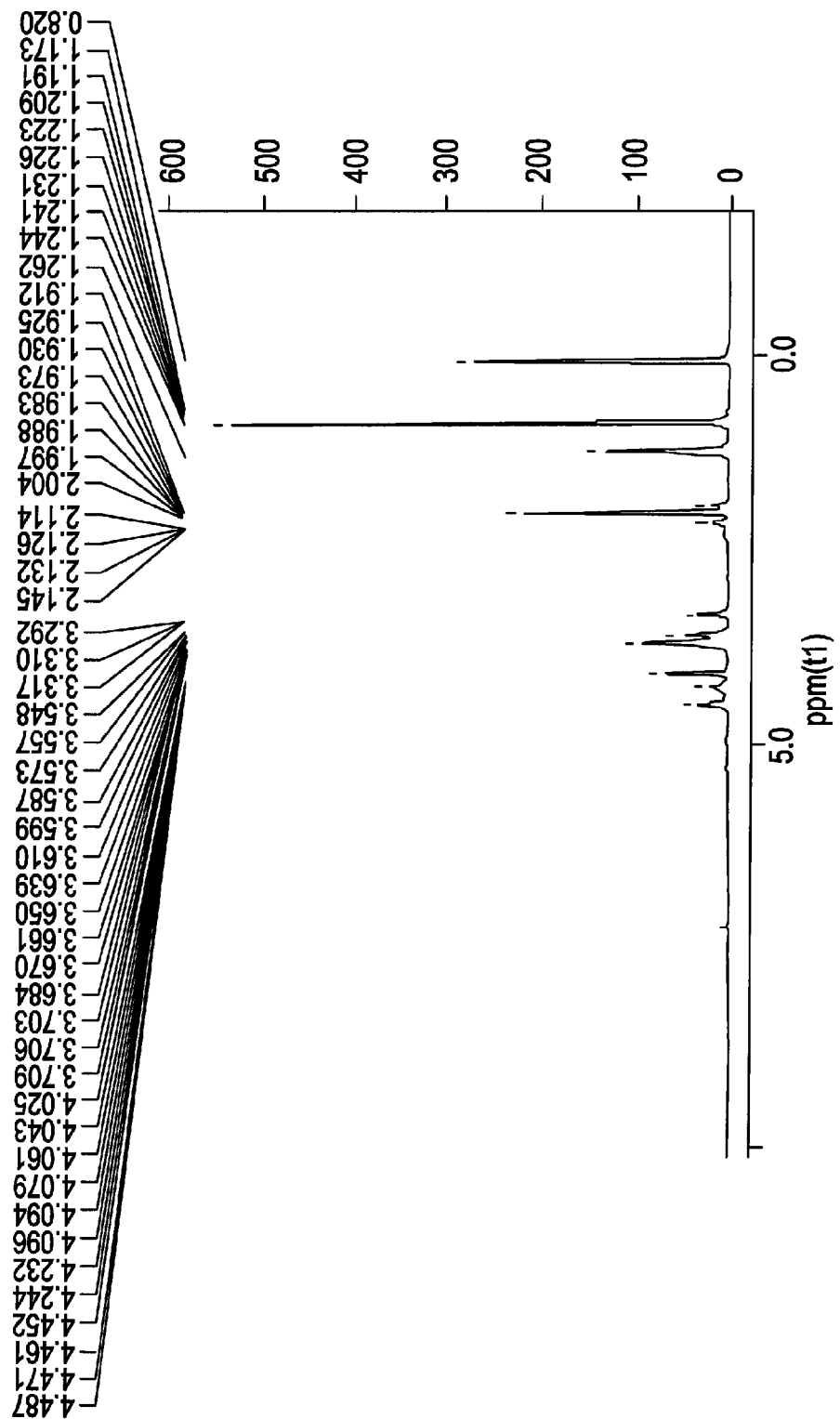
FIG. 10 is a proton nuclear magnetic resonance spectrum of biomonomer POC-TEG-POC (protected oxaceprol-triethylene glycol-protected oxaceprol).

$^1$H NMR: (400 MHz, CDCl$_3$) δ: 4.87 (m, 2H, CHCO$_2$), 4.26 (m, 2H, CHOSi), 4.05 (m, 2H, CHHN), 3.74-3.31 (m, 4H), 3.31 (m, 2H, CHHN), 2.13 (m, 4H, CH$_2$CHCO$_2$), 2.12 (s, 6H, COCH$_3$), 2.0 (m, 4H), 1.18 (m, 4H), 0.81 (s, 18H, C(CH$_3$)$_3$), −0.003 (s, 6H, SiCH$_3$), −0.03 (s, 6H, SiCH$_3$). [FIG. 10]

Figure 11:
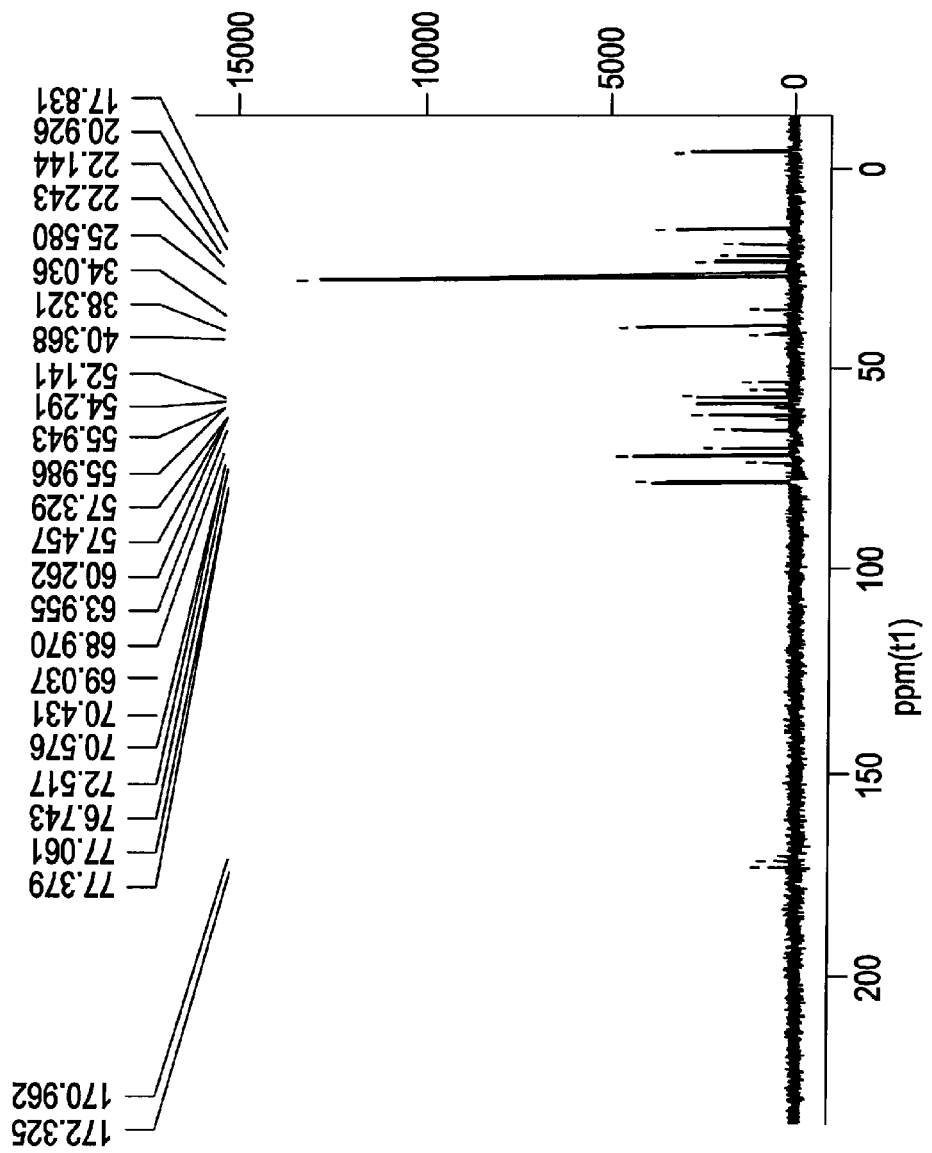
FIG. 11 is a carbon nuclear magnetic resonance spectrum of biomononer of POC-TEG-POC.

$^{13}$C NMR: (400 MHz, CDCl$_3$) δ: 172.3, 171.0, 72.5, 70.6, 70.4, 64.0, 60.3, 57.5, 57.3, 55.9, 54.3, 52.1, 40.4, 38.3, 34.0, 26.6, 22.1, 20.9, 17.8, 14.1, −4.8, −5.0. [FIG. 11]

Figure 12:
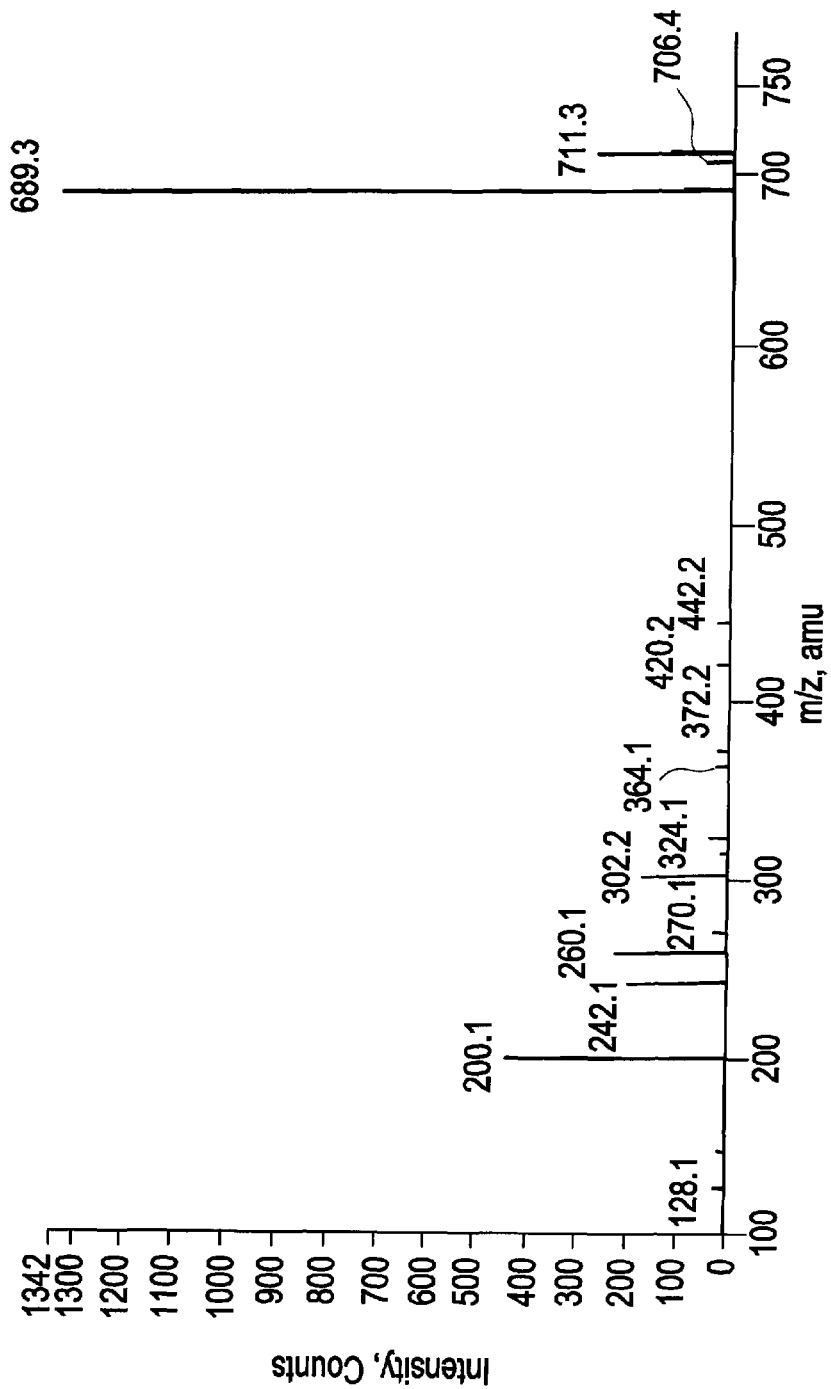
FIG. 12 is a positive electrospray mass spectrum of POC-TEG-POC.

ES-MS (m/z, %) (Positive mode): Calculated for mass C$_{32}$H$_{60}$N$_2$O$_{10}$Si$_2$: 688 amu. found 689.3. [FIG. 12]

In step D, the purified product C (0.7 mmol) was dissolved in THF (5 ml). The resulting solution was cooled to 0° C. before the addition of tetra n-butyl ammonium fluoride (x ml, 1.4 mmol). The resulting solution was stirred at 0° C. for 5 min before the removal of the ice bath and continued stirring for an additional 40 min at ambient temperature. The solvent was removed at reduced atmosphere and the residue was treated with water and the pH of the solution was adjusted to 3 upon which a precipitate resulted. The precipitate was filtered to produce the desired product.

Example 5

TF-TEG-TF is an example of anti-thrombic drug containing biomonomer according to the invention. The biomonomer is synthesized using tirofiban (TF), reacting the carboxylic acid with the hydroxyl of TEG and leaving the amines for subsequent use in the polymerization. The conditions for synthesis for this reaction are as follows.

In step A, TF (4 mmol) is reacted with trityl chloride (8.8 mmol) and TEA (8 mmol) (Aldrich, 99%) in 40 ml of CHCl$_3$ for four hours at room temperature. A clear solution is obtained.

In step B, 40 ml of methanol is added into the above clear solution. The mixture is heated to 50° C. and stirred for one hour, a lot of precipitates appeared in the solution. After the reaction mixture is cooled down to room temperature, precipitates were collected by filtration. They were further purified from CHCl$_3$/methanol. 3.4 mmol of Product B were obtained.

In step C, Product B (20 mmol), TEG (9.S mmol), DMAP (1.24 g, 10 mmol) were dissolved in 100 ml DCM. EDAC (31 g, 160 mmol) is added into the reaction system. The reaction mixture is stirred at room temperature under a nitrogen atmosphere for one week. After reaction is finished, DCM was removed by rotary evaporator. The residues were washed with de-ionized water several times to remove soluble reagents such as the by-product of urea. The solids were then dissolved in chloroform and washed with de-ionized water again. The crude product of the reaction is recovered from the solution by extraction. Product C was isolated by column chromatography using the developer of chloroform/methanol/ammonia hydroxide aqueous solution (9.2:0.6:0.2). Product C is further purified with recrystallization technique from chloroform and methanol.

In step D, the purified product C (4 mmol) is dissolved in chloroform containing one volume percent of water and 1 volume percent of trifluoroacetic acid. The reaction solution is stirred at room temperature for 4 hrs. White precipitates produced in the reaction were collected by filtration and purified by washing with chloroform. Following washing Product D, i.e. the biomonomer is dried in vacuum oven for 24 hours at a temperature of 40° C.

Example 6

AK-TEG-AK is an example of anti-proliferation drug containing biomonomer according to the invention. The biomonomer was synthesized using Alkeren (AK), reacting the carboxylic acid with the hydroxyl of TEG and leaving the amines for subsequent use in the polymerization. The conditions for synthesis for this reaction are as follows.

In step A, AK (0.32 mmol) was reacted with di-tert-butyl carbonate (0.5 mmol) and TEA (0.32 mmol) (Aldrich, 99%) in THF (4 ml). The suspension was cooled to 0° C. before the addition of the anhydride. Dimethylformamide (0.9 ml) was added to homogenize the reaction mixture. The solution was stirred for 2 hours at 0° C., and thereafter overnight at ambient temperature. The solution is then evaporated under reduced pressure and the yellowish-oily residue obtained is redissolved in a 5% aqueous solution of sodium bicarbonate (3 ml). The solution is washed with petroleum ether (3×3 ml) and the aqueous phase was acidified to a pH of 3 with a 1 N hydrochloric acid solution. The mixture was extracted with ethyl acetate (3×3 ml). The organic phases were dried over anhydrous sodium sulfate, filtered and then evaporated under reduced pressure. The residue is dissolved in a mixture of hexane, ethyl acetate, and acetic acid (20:10:1) (3 ml). It is subsequently purified by chromatography on a silica column. This produced 115 g (86%) of the desired product (R$_f$=0.49).

Figure 13:
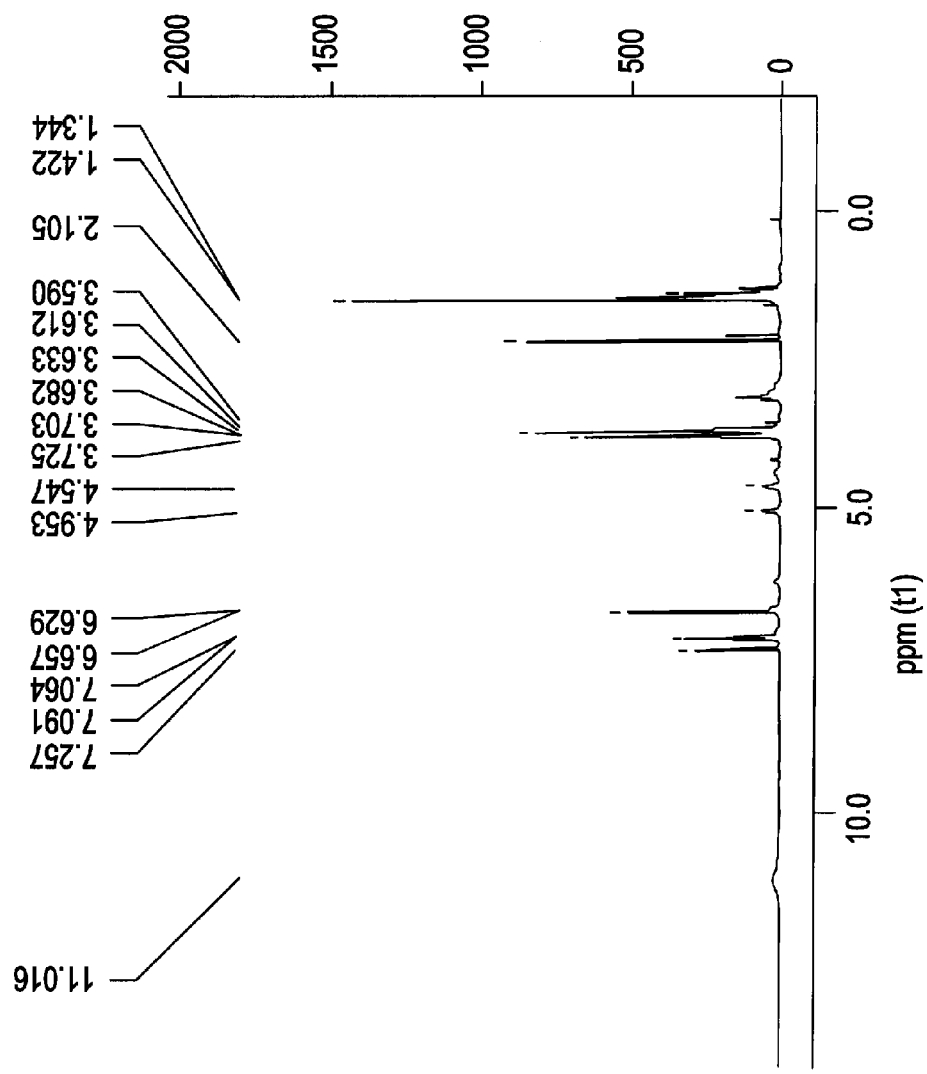
FIG. 13 is a proton nuclear magnetic resonance spectrum of PAK (protected alkeren).

$^1$H NMR: (400 MHz, CDCl$_3$) δ: 11.02 (bs, 1H, CO$_2$H), 7.08 (d, 2H, J=5.4 Hz, Ar—H), 6.64 (d, 2H, J=5.4 Hz, Ar—H), 4.97 (d, 1H, J=5 Hz, NH), 4.57 (m, 1H, CHCO$_2$H), 3.72-3.59 (m, 8H, CH$_2$CH$_2$Cl), 3.12-2.98 (m, 2H, CH$_2$CH), 1.42 (s, 9H, C(CH$_3$)$_3$). [FIG. 13]

Figure 14:
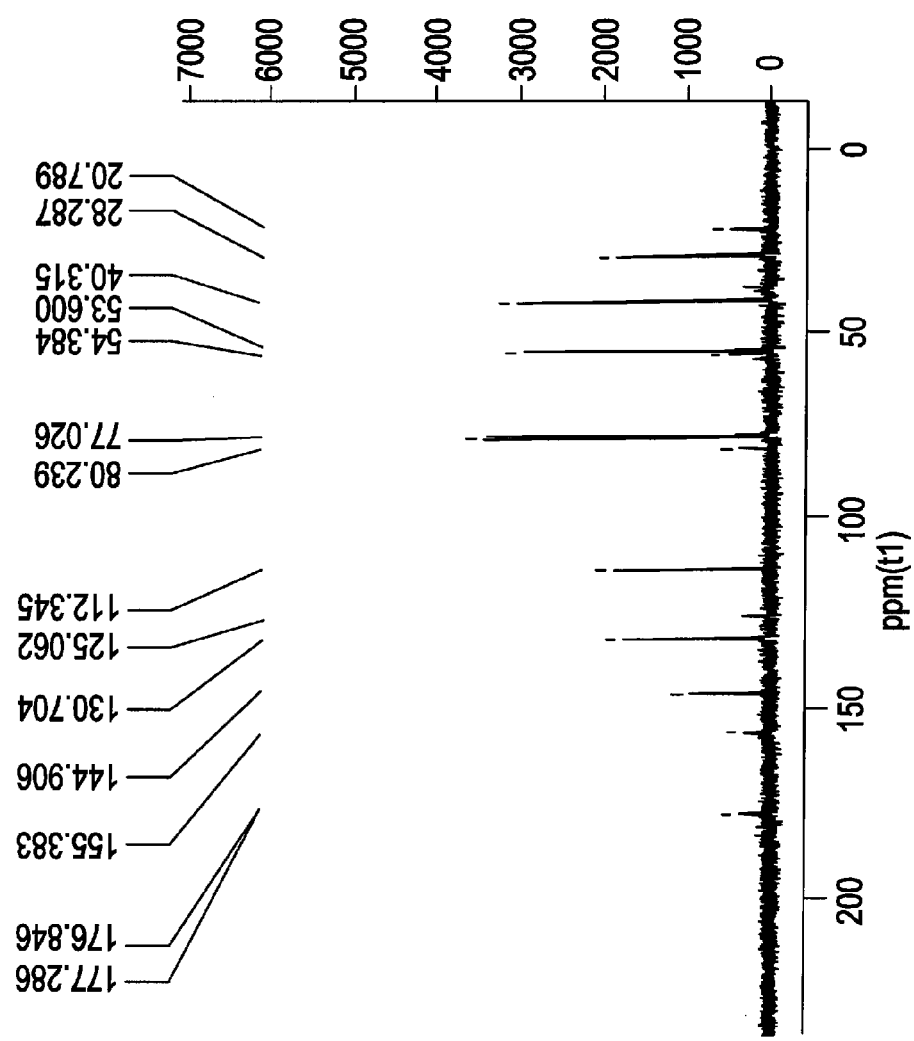
FIG. 14 is a carbon nuclear magnetic resonance spectrum of PAK

$^{13}$C NMR: (400 MHz, CDCl$_3$) δ: 177.3, 176.6155.4, 144.9, 130.7, 112.3, 80.2, 54.4, 53.6, 40.3, 28.3, 20.8. [FIG. 14]

Figure 15:
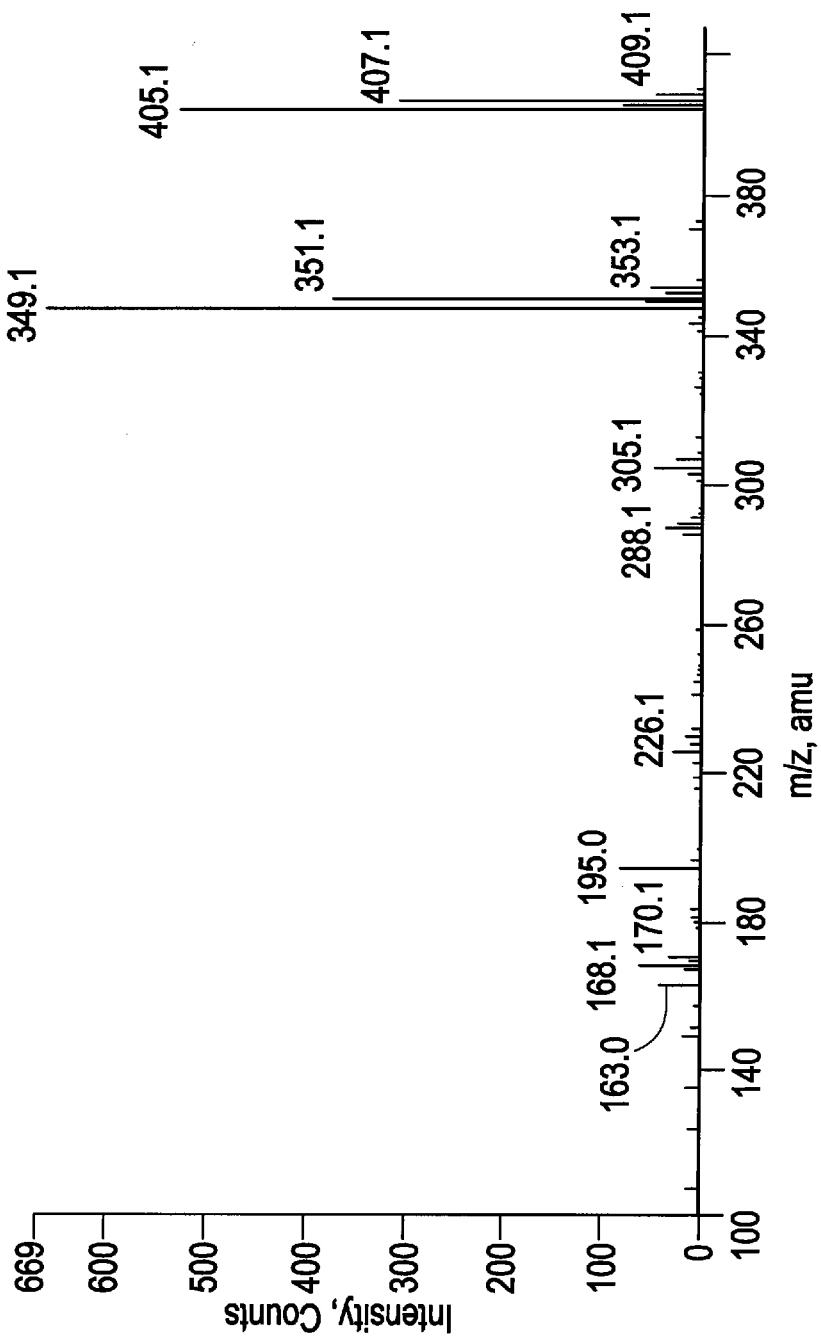
FIG. 15 is a positive electrospray mass spectrum of PAK

ES-MS (m z, %) (Positive mode): Calculated for mass C$_{18}$H$_{26}$Cl$_2$N$_2$O$_4$: 404 amu. found 405.1. [FIG. 15]

In step C, Product B (0.20 mmol), TEG (0.09 mmol), DMAP (0.009 mmol) were dissolved in DCM (2 ml). To this stirring solution at 0° C. was added EDC-HCl (0.22 mmol) in dichloromethane (1 ml) dropwise over 10 min. The resulting solution was stirred for 1 h at 0° C., the cooling was removed, and the mixture was stirred for 3 days at ambient temperature. The progress of the reaction was monitored by thin layer chromatography. Once complete disappearance of starting material was observed, the reaction solvent was removed under reduced atmosphere. The product was purified by column chromatography (R$_f$=0.93) eluting with chloroform: methanol (9:1). This produced 0.8 g (73%) of the desired product.

$^1$H NMR: (400 MHz, CDCl$_3$) δ: 7.03 (d, 4H, J=5.4 Hz, Ar—H), 6.64 (d, 4H, J=5.4 Hz, Ar—H), 4.98 (d, 2H, J=5.0 Hz, NH), 4.55 (m, 2H, CHCO$_2$H), 4.28 (m, 4H, CO$_2$CH$_2$)

Figure 16:
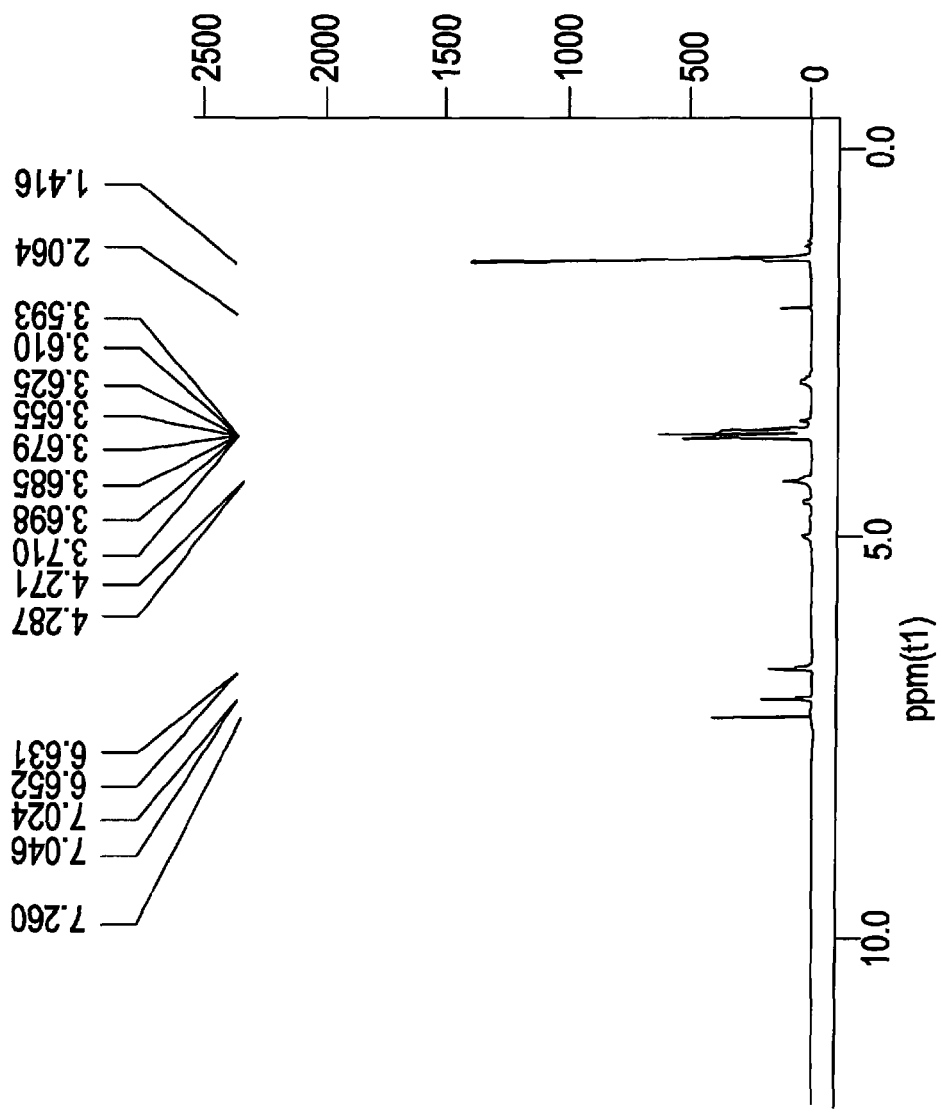
FIG. 16 is a proton nuclear magnetic resonance spectrum of biomononer PAK-TEG-PAK (protected alkeren-triethylene glycol-protected alkeren).

3.72-3.59 (m, 24H, $CH_2CH_2Cl$, $OCH_2CH_2OCH_2$), 3.06-2.95 (m, 4H, $CH_2CH$), 1.42 (s, 18H, $C(CH_3)_3$). [FIG. 16]

Figure 17:
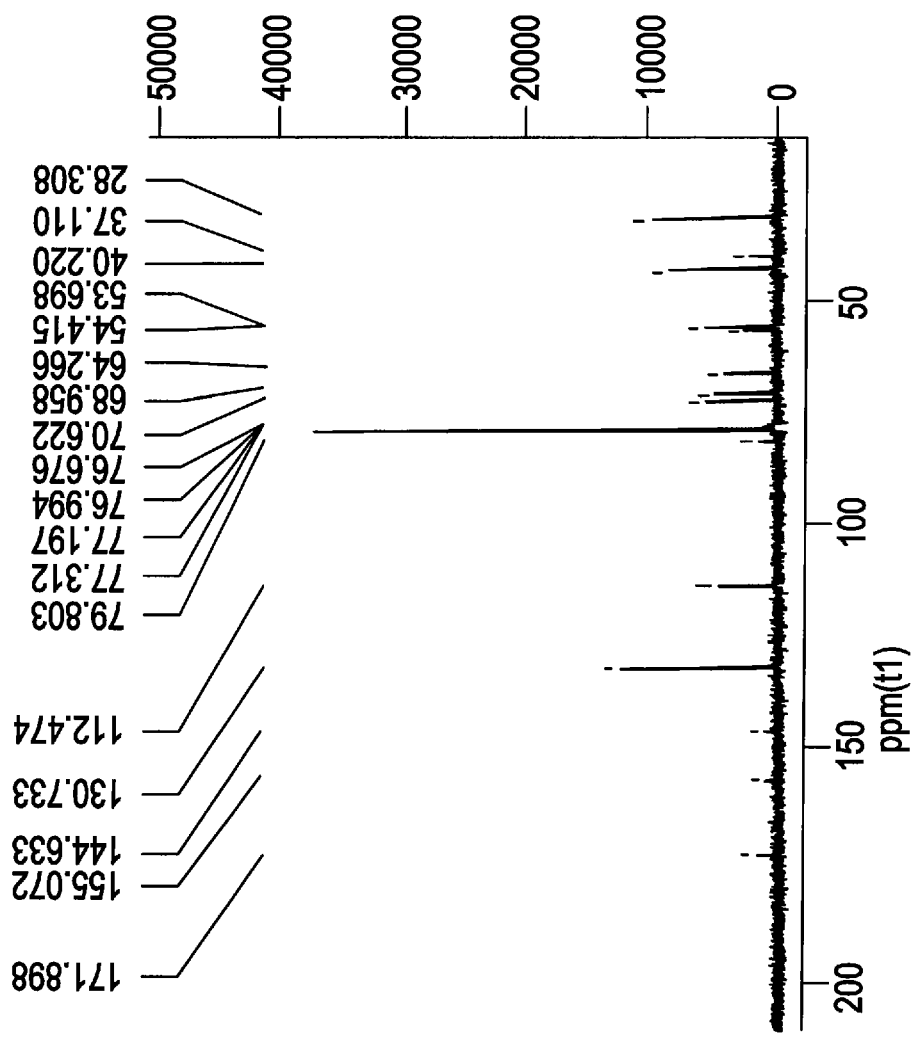
FIG. 17 is a proton nuclear magnetic resonance spectrum of biomononer PAK-TEG-PAK

$^{13}C$ NMR: (400 MHz, $CDCl_3$) δ: 177.3, 171.9, 155.0, 144.6, 130.7, 112.5, 79.8, 70.6, 69.0, 64.3, 54.4, 53.7, 40.2, 37.1, 28.3. [FIG. 17]

Figure 18:
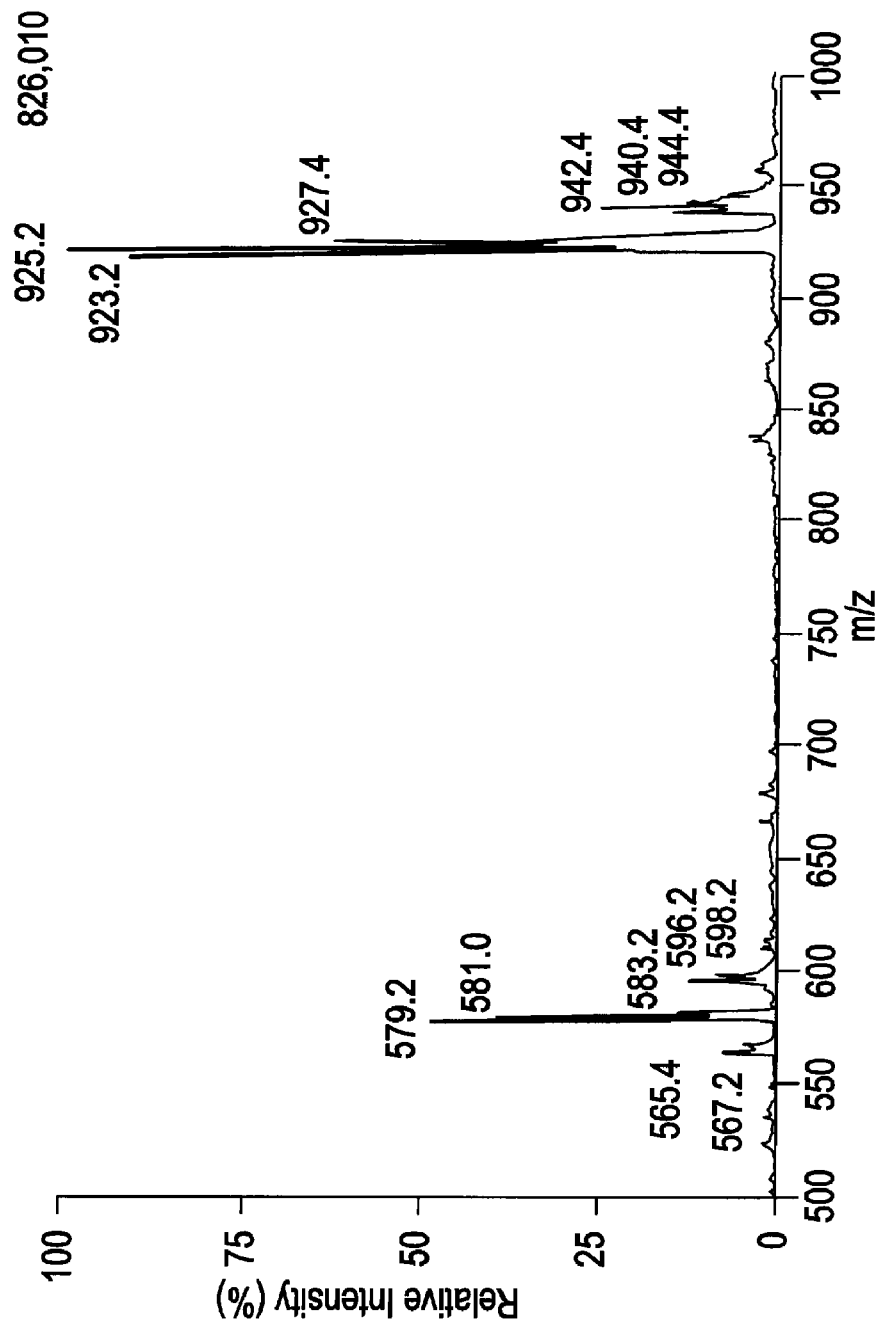
FIG. 18 is a positive electrospray mass spectrum of biomononer PAK-TEG-PAK
Figure 19:
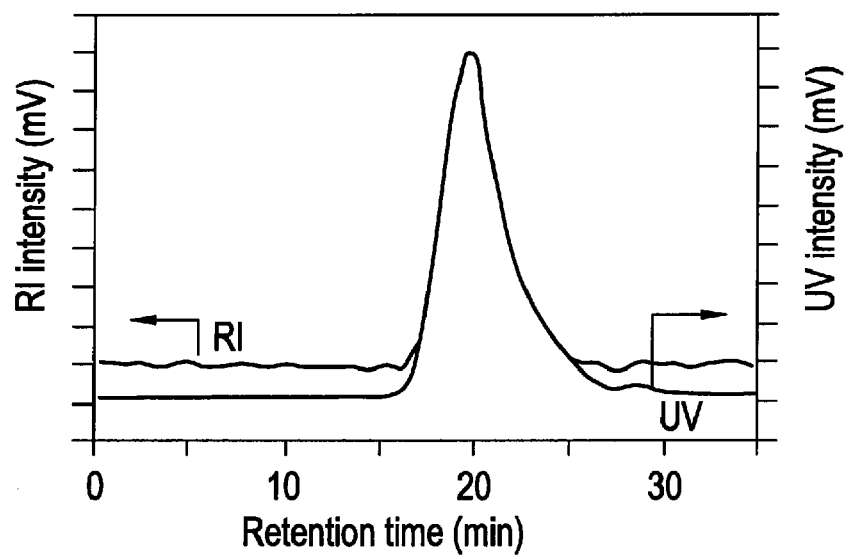
FIG. 19 is a gel permeation chromatography analysis of THDI/PCL/NORF (trimethyl-1,6 diisocyanatohexane-polycarprolactone diol-norfloxacin).
Figure 20:
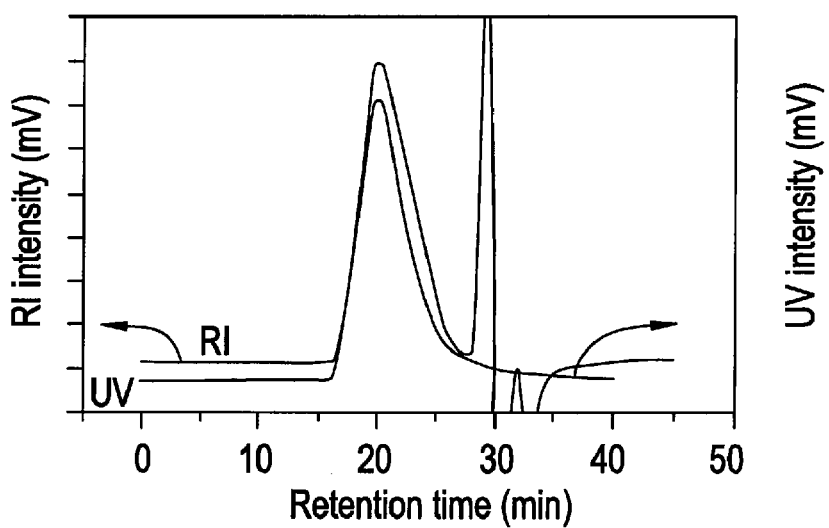
FIG. 20 is a gel permeation chromatography analysis of THDI/PCL/CIPRO (trimethyl-1,6 diisocyanatohexane-polycarprolactone diol-ciprofloxacin)
Figure 21:
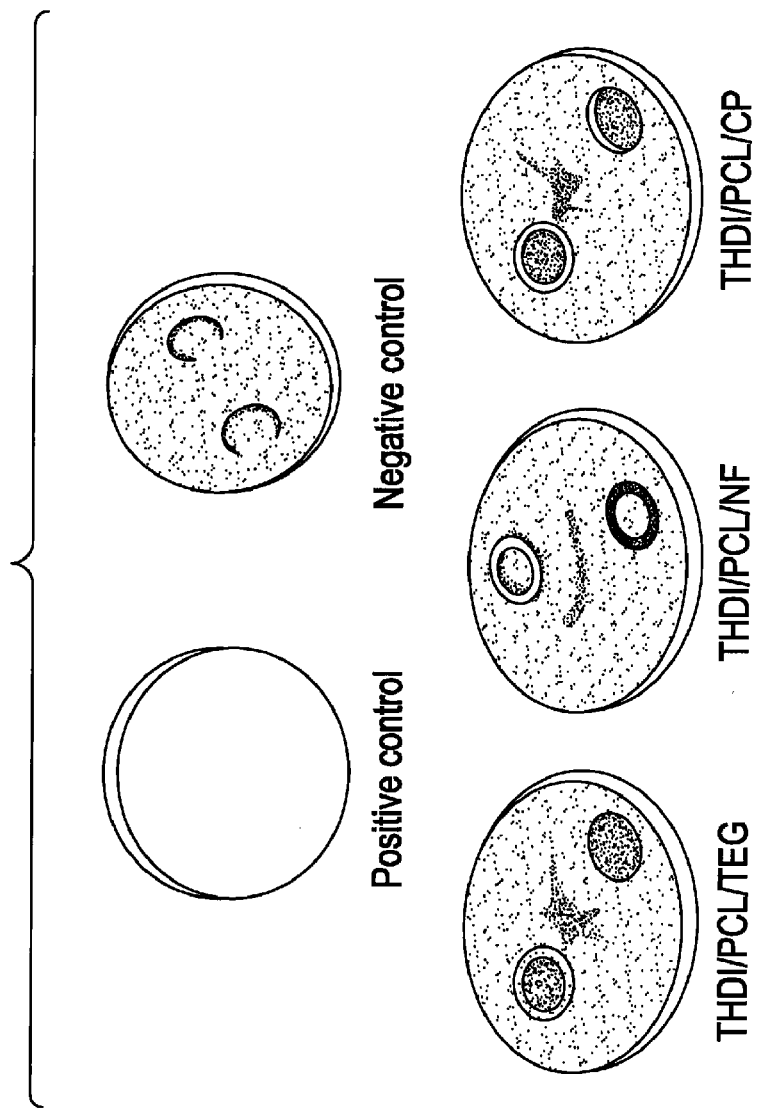
FIG. 21 is a cytotoxicity test of control polymer and drug polymers with mammalian cells.
Figure 22:
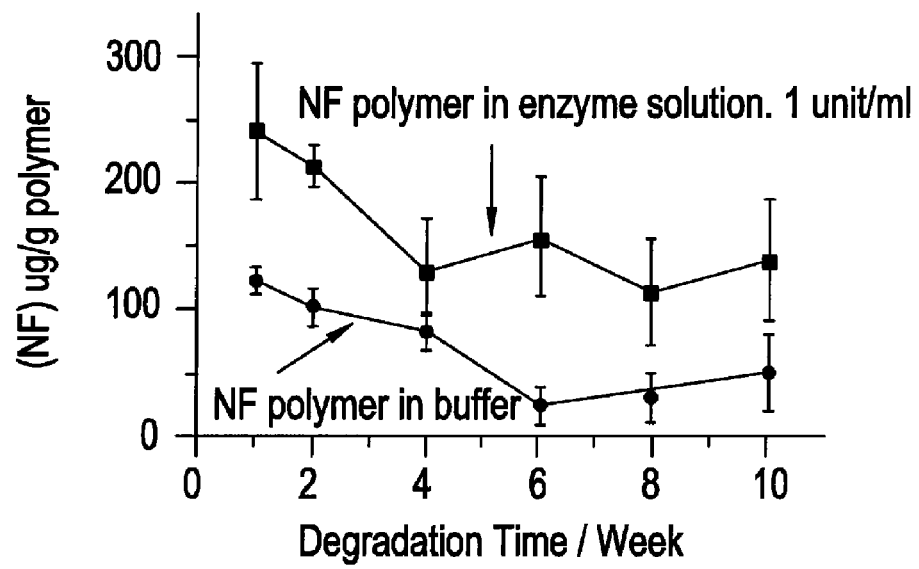
FIG. 22 is a graph of the released norfloxacin from NF polymer in the presence and absence of cholesterol esterase.
Figure 23:
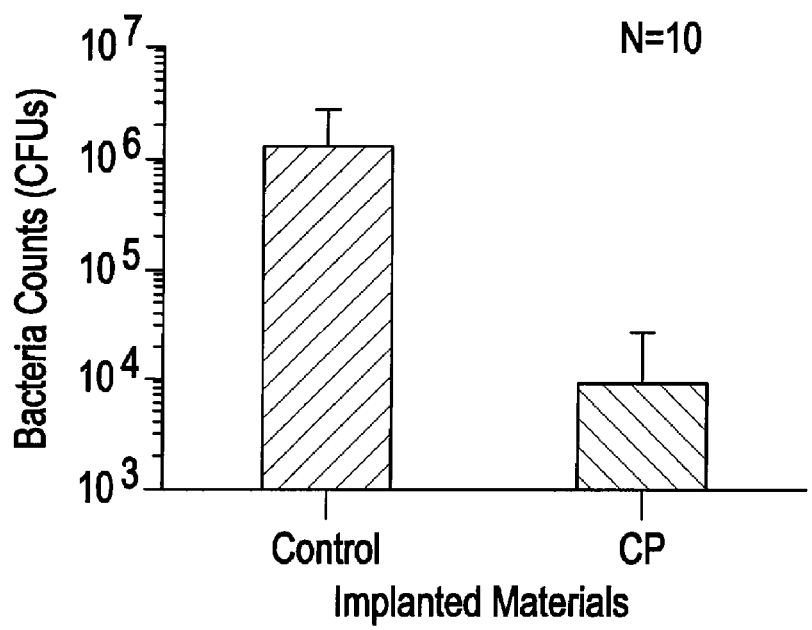
FIG. 23 is a graph of bacteria counts from implanted coupons.

ES-MS (m/z, %) (Positive mode): Calculated for mass $C_{42}H_{62}Cl_4NO_{10}$: 922 amu. found 923.2. [FIG. 18]

In step D, the purified product C (2 mmol) was dissolved in chloroform containing one volume percent of water and 1 volume percent of trifluoroacetic acid. The reaction solution was stirred at room temperature for 2 hrs. White precipitates produced in the reaction were collected by filtration and purified by washing with chloroform. Following washing Product D, i.e. the biomonomer was dried in vacuum oven for 24 hours at a temperature of 40° C.

Example 7

THDI/PCL/NORF is an example of pharmaceutically active polyurethane containing 15% of drugs according to the invention. The conditions of synthesis for this reaction are as follows.

1.5 grams of PCL are reacted with 0.27 grams of THDI in the presence of 0.06 ml of the catalyst, dibutyltin dilaurate, in a nitrogen atmosphere with in dimethylsulfoxide (DMSO) (10 mL) for one hour. The reaction temperature is maintained between 60-70° C. 0.32 grams of NORF-TEG-NORF is dissolved in 5 ml DMSO was then added into reaction system. The reaction is keep at 60-70° C. for 5 hours and then at room temperature for overnight. Reaction is finally stopped with 1 ml of methanol. The final drug polymer is precipitated in a mixture of ether/water (50 v/v %). The precipitated polymer is then dissolved in acetone and precipitated in ether again. This washing procedure is repeated three times.

Figure 5:
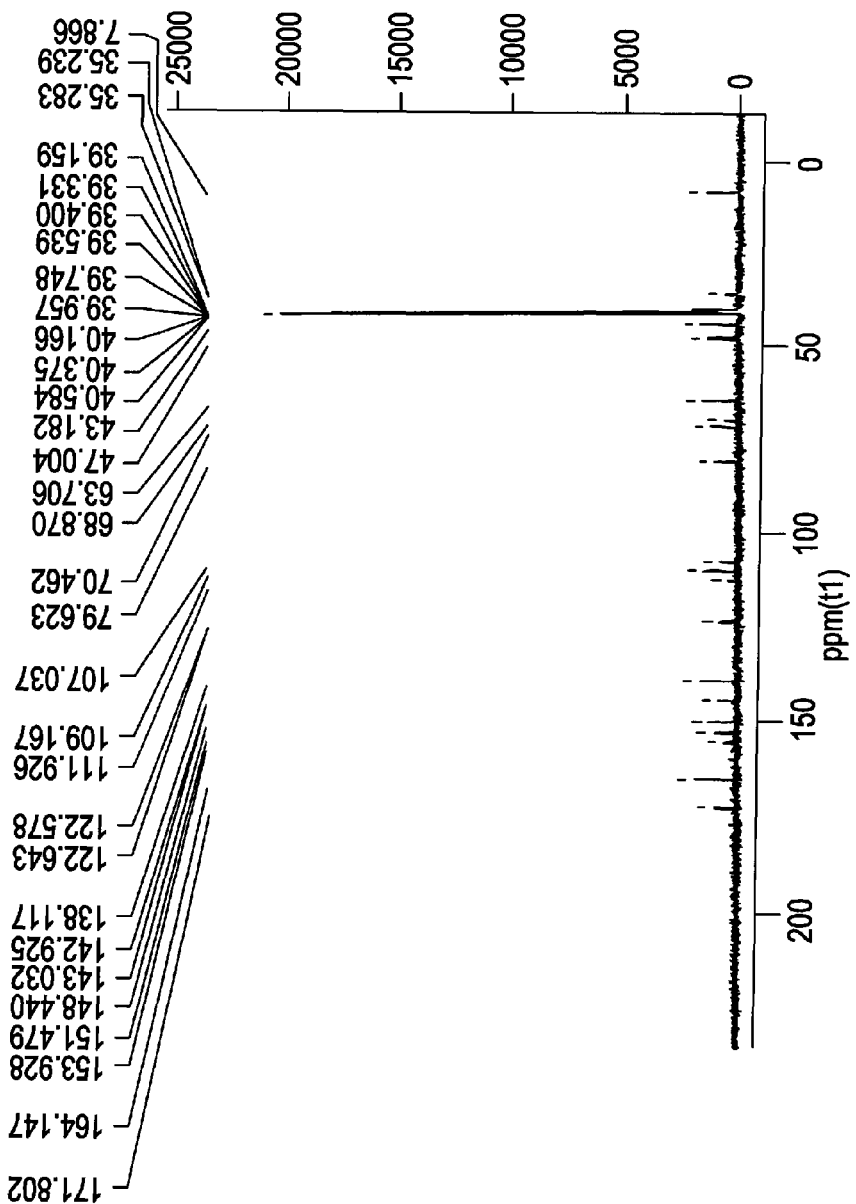
FIG. 5 is a carbon nuclear magnetic resonance spectrum of biomonomer of CIPRO-TEG-CIPRO.

Norfloxacin is the only component in the drug polymer which has a strong detectable absorbance at 280 nm in the UV range. Hence, its presence can be detected using a UV detector. FIG. 5 super-imposes the UV chromatogram for the drug polymer with its universal gel permeation chromatography (GPC) curves using a universal refractive index detector. Similar data is shown for a Ciprofloxacin polymer in FIG. 6. The latter detects the presence of all molecules because it has a dependence on mass of material present, eluting out of the GPC column at a specific time. Hence, a comparison of the two signals shows that the distribution of norfloxacin is identical to the distribution of actual molecular weight chains, meaning that there was no preferential coupling of norfloxacin/ciprofloxacin to low versus high molecular weight chains or vice-versa; implies that the coupling of norfloxacin/ciprofloxacin was uniform.

Example 8

AC/CIPRO is an example of pharmaceutically active polyamide containing antimicrobial drug Ciprofloxacin according to the invention. It differs from example 1 in that it is not a polyurethane and shows the versatility for the use of the biomonomers in a range of step growth polymerizations. The conditions for this synthesis are a common polyamide interfacial polycondensation reaction. They are described as follows:

A solution of 3.88 g (5 mmol) of CIPRO-TEG-CIPRO and 1.06 g (10 mmol) of sodium carbonate in 30 ml of water was cooled in an ice bath for 15 min before addition of as the water phase to a 150 ml flask containing a stir bar. A organic solution containing 0.915 g of adipoyl chloride (AC, 5 mmol) in 20 ml of methylene chloride was added slowly into the water phase under vigorously stirring. The organic solution has been previously cooled in an ice bath for 15 min. Immediately after addition of the organic phase, an additional 5 ml of methylene chloride was used to rinse the original acid chloride container and transfer the solvent to reaction flask. The polymerization medium was stirred at maximum speed for an additional 5 min. The resulting polymer was collected by filtration. The polymer was then washed with water for at least 3 times. It was then washed with acetone twice. The product was vacuum-dried at 40° C. for 24 hours.

Example 9

Gamma irradiation is a popular and well-established process for sterilizing polymer-based medical devices (21). It has been known, however, that this technique can lead to significant alterations in the materials being treated. High-energy radiation produces ionization and excitation in polymer molecules. The stabilization process of the irradiated polymer results in physical and chemical cross-linking or chain scission, which occurs during, immediately after, or even days, weeks after irradiation. In this example, NF and CP polymers are dissolved in a suitable solvent such as chloroform at 10%. The films are cast in a suitable holder such as Teflon mold and placed in a 60° C. air flowing oven to dry. The dried films are sterilized by gamma radiation. The dose shall be capable of achieving the pre-selected sterility assurance level (22), One of two approaches shall be taken in selecting the sterilization dose: (a) selection of sterilization dose using either 1) bioburden information, or 2) information obtained by incremental dosing; b) Selection of a sterilization dose of 25 Kgy following substantiation of the appropriateness of this dose. Each sample had twelve films (N=3) to be sterilized by Gamma radiation. Resultant chemical changes can be detected at different time points as follow: a) No sterile (3); b) Immediately after irradiation (3); c) Two weeks after irradiation (3); d) 1 month after irradiation (3). After Gamma sterilization, the films are analyzed by GPC to detect the change in the number-averaged molecular weight (Mn), weight-averaged molecular weight (Mw), and polydispersity (Mw/Mn) of polymer chains before and after radiation. The results are listed in Table 3. It shows that no obvious physical and chemical changes happened to the drug polymers after radiation sterilization.

TABLE 3

Mn, Mw, and Polydispersity of drug polymers before and after Radiation

| Samples | Mn g/mol | Mw g/mol | PI |
|---|---|---|---|
| THDI/PCL/NF: | | | |
| A: | $2.2 \times 10^4$ | $6.9 \times 10^4$ | 2.1 |
| B: | $3.2 \times 10^4$ | $6.2 \times 10^4$ | 2.1 |
| C: | $3.0 \times 10^4$ | $6.4 \times 10^4$ | 2.1 |
| Right after radiation: | | | |
| A: | $3.0 \times 10^4$ | $6.2 \times 10^4$ | 2.0 |
| B: | $2.9 \times 10^4$ | $6.2 \times 10^4$ | 2.0 |
| C: | $3.2 \times 10^4$ | $6.3 \times 10^4$ | 2.0 |
| 1 week after radiation | | | |
| A: | $2.9 \times 10^4$ | $6.0 \times 10^4$ | 2.1 |
| B: | $3.1 \times 10^4$ | $6.7 \times 10^4$ | 2.2 |
| C: | $2.8 \times 10^4$ | $6.0 \times 10^4$ | 2.1 |

TABLE 3-continued

Mn, Mw, and Polydispersity of drug polymers before and after Radiation

| Samples | Mn g/mol | Mw g/mol | PI |
|---|---|---|---|
| 2 weeks after radiation | | | |
| A: | $2.9 \times 10^4$ | $6.0 \times 10^4$ | 2.1 |
| B: | $3.0 \times 10^4$ | $6.4 \times 10^4$ | 2.1 |
| C: | $3.0 \times 10^4$ | $6.3 \times 10^4$ | 2.1 |
| 1 month after radiation | | | |
| A: | $2.8 \times 10^4$ | $6.1 \times 10^4$ | 2.1 |
| B: | $2.8 \times 10^4$ | $5.8 \times 10^4$ | 2.1 |
| C: | $2.8 \times 10^4$ | $5.9 \times 10^4$ | 2.1 |
| THDI/PCL/CP: | | | |
| A: | $2.1 \times 10^4$ | $3.4 \times 10^4$ | 1.6 |
| B: | $2.1 \times 10^4$ | $3.3 \times 10^4$ | 1.6 |
| C: | $2.1 \times 10^4$ | $3.3 \times 10^4$ | 1.6 |
| Right after radiation: | | | |
| A: | $2.1 \times 10^4$ | $3.4 \times 10^4$ | 1.6 |
| B: | $2.3 \times 10^4$ | $3.6 \times 10^4$ | 1.6 |
| C: | $2.3 \times 10^4$ | $3.7 \times 10^4$ | 1.6 |
| 1 week after radiation | | | |
| A: | $2.3 \times 10^4$ | $4.0 \times 10^4$ | 1.6 |
| B: | $2.2 \times 10^4$ | $3.6 \times 10^4$ | 1.6 |
| C: | $2.2 \times 10^4$ | $3.7 \times 10^4$ | 1.6 |
| 2 weeks after radiation | | | |
| A: | $2.2 \times 10^4$ | $3.7 \times 10^4$ | 1.7 |
| B: | $2.2 \times 10^4$ | $3.6 \times 10^4$ | 1.7 |
| C: | $2.2 \times 10^4$ | $3.9 \times 10^4$ | 1.7 |
| 1 month after radiation | | | |
| A: | $2.1 \times 10^4$ | $3.4 \times 10^4$ | 1.7 |
| B: | $2.1 \times 10^4$ | $3.6 \times 10^4$ | 1.7 |
| C: | $2.1 \times 10^4$ | $3.5 \times 10^4$ | 1.7 |

Example 10

This example shows the in vitro cytotoxicity of a non-bioactive control polymer, NF and CP polymers with mammalian cell lines using a direct contact method. In this method, 1 ml of polymer DMSO solutions containing 1 mg/ml, 3 mg/ml and 5 mg/ml, respectively, of control or drug polymer is loaded on each Millipore 0.45 μm filter that is set on top of agar in a Petri dish. These dishes are then incubated at 37° C. in a humidified atmosphere of 5% $CO_2$ for 24 hours. After the solvent is diffused into agar, these filters with polymers loaded on it are transferred into a new Petri dish containing solidified agar. HeLa cells are seeded onto these filters. The dishes are incubated at 37° C. in a humidified atmosphere of 5% $CO_2$ for 48 hours. Cells are stained with succinic dehydrogenase staining buffer. The stained areas on the filters show the cytotoxicity of materials. FIG. 7 show the scanned pictures of stained cells that are seeded on the filters loaded with different amounts of control, NF and CP polymers. There are no unstained areas in each filter. The results show that the control polymer and bioactive polymers have good biocompatibility with mammalian cells.

Example 11

Figure 8:
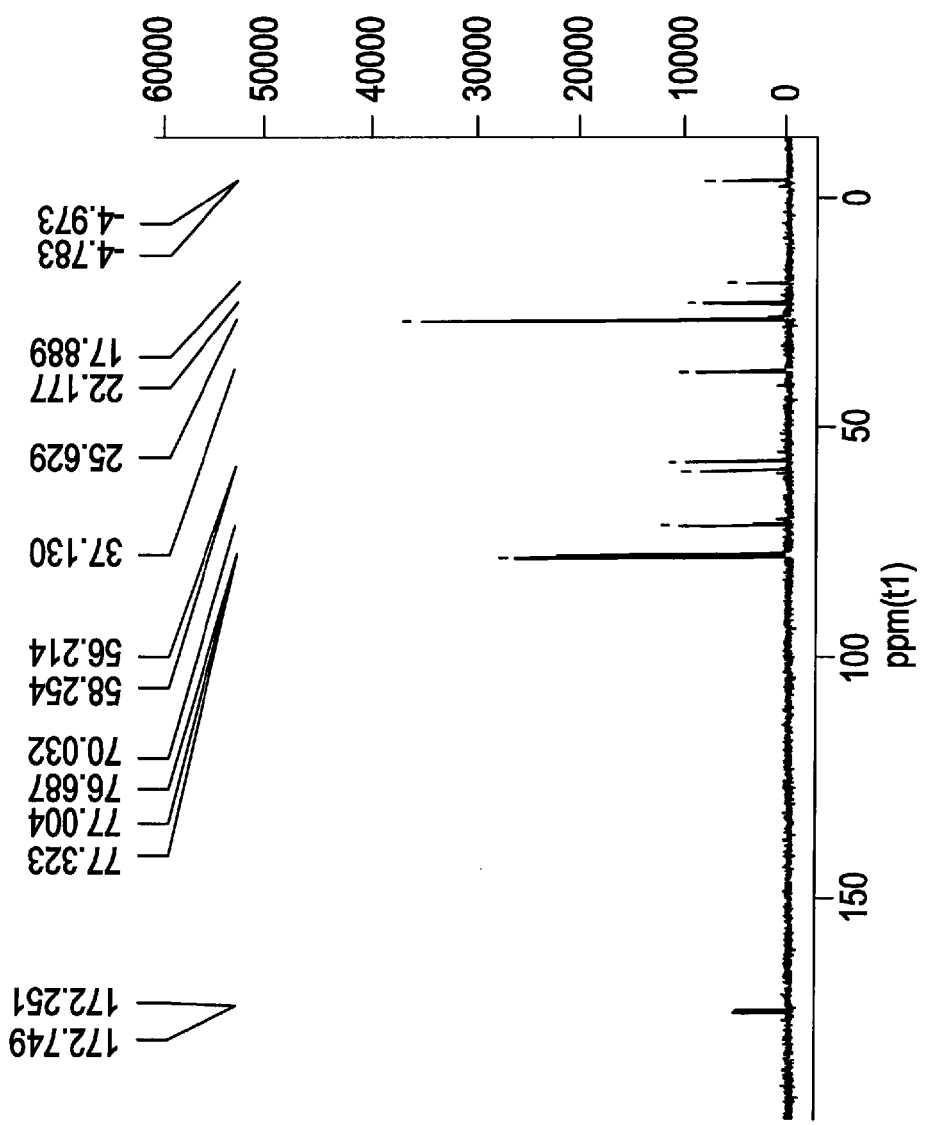
FIG. 8 is a carbon nuclear magnetic resonance spectrum of POC.

NF polymer was used to evaluate the ability of a hydrolytic enzyme to degrade the material, and preferentially release drug. NF polymer was coated onto small glass cylinders, and then incubated in the presence and absence of hydrolytic enzyme (i.e. cholesterol esterase) for up to 10 weeks at 37° C. At each week interval the incubation solution was removed from NF polymer and fresh enzyme solution was added. The incubation solutions were assayed via high pressure liquid chromatography (HPLC). Standard solutions of pure norfloxacin were run through an HPLC system to get calibration curve of this system. Norfloxacin concentration in the incubated solution was determined by comparison of drug peak area of incubation solution to calibration curve. FIG. 8 shows the released norfloxacin from NF polymer in the presence and absence of cholesterol esterase. In the presence of CE, there is an obvious release of Norfloxacin 10 weeks. However in the absence of CE, there only is some release of drug in the first 6 weeks and it is lower than that of the enzyme incubated samples throughout the experiment.

The same NF polymer incubation solutions assayed via HPLC were also evaluated for antimicrobial activity using a biological assay. A macro-dilution minimum inhibitory concentration (MIC) assay was employed to determine the concentration of antimicrobial (norfloxacin) that would inhibit the growth of a pathogen often associated with device-related infections, *Pseudomonas aeruginosa*. The MIC for this organism and norfloxacin was determined to be 0.8 mu g/mL. Incubation solutions from both enzyme and buffer control treatment of NF polymer were used in a biological assay matrix that was designed to estimate the concentration of norfloxacin as a function of incubation time and treatment. The data are presented in Table 4. Anti-microbial activity was not detected in the NF polymer exposed to buffer (control) incubation solution after 2 weeks. However, the enzyme-treated NF polymers released clinically significant levels (>MIC levels) of antibiotic over a 10 week incubation period. These biological assay data show a significant correlation with the HPLC data described above. The results of these experiments demonstrate that the antibiotic agent is released from NF polymer under enzymatic activation, and that the antibiotic has antimicrobial activity against a clinically significant bacterium. Furthermore, clinically significant concentrations (i.e., MIC level) of the antibiotic are released over an extended period of time, 10 weeks.

TABLE 4

MIC Assay for antibacterial activity of degraded NF polymer solutions. Samples containing drugs greater than or less than MIC level

| | Sample No. | | | | | | | |
|---|---|---|---|---|---|---|---|---|
| | 1 | 2 | 3 | 4 | 5 | 6 | 7 | 8 |
| | | | | | Solution | | | |
| Time | CE | CE | CE | CE | buffer | buffer | buffer | buffer |
| 1 week | > | > | > | > | > | > | > | > |
| 2 weeks | > | > | > | > | > | > | > | > |
| 3 weeks | > | > | > | > | < | > | < | < |
| 4 weeks | > | > | > | > | < | > | < | < |
| 6 weeks | > | > | > | > | < | < | < | < |
| 8 weeks | > | > | > | > | < | < | < | < |
| 10 weeks | > | > | > | > | < | < | < | < |

Example 13

Figure 9:
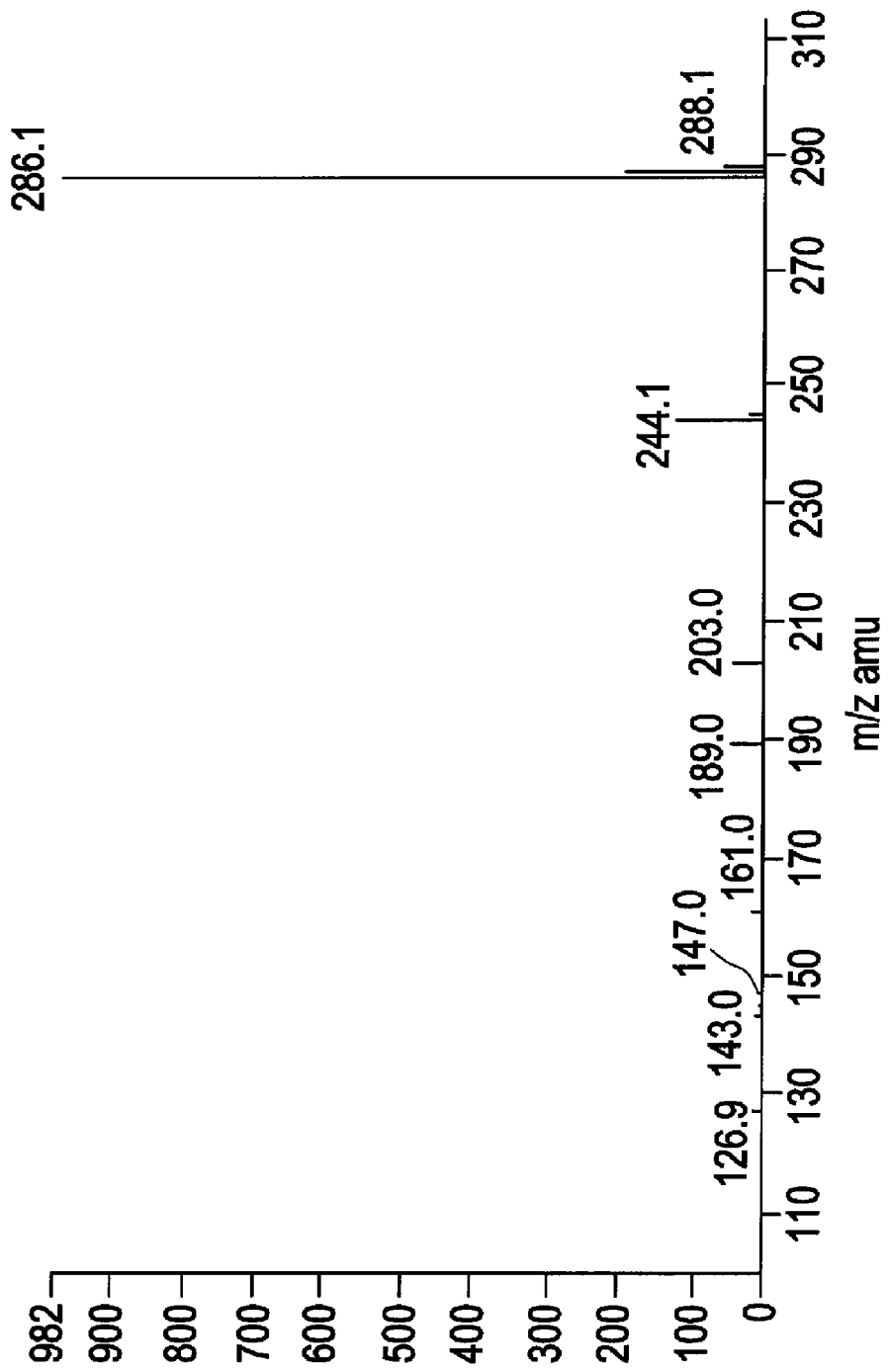
FIG. 9 is a positive electrospray mass spectrum of POC.

In vivo animal studies are performed on formed coupons made of control and CP polymer with a dimension of 1×2 $cm^2$. The coupons were implanted in the peritoneal cavity of male rats. The coupons were explanted after rats were housed for 1 week. The experimental conditions according to the invention are as follows:

For implantation, 5 male Sprague-Dawley rats (250-300 g) were used for every group of experiment. After they were anesthetised, a 2 cm laparotomy incision was made in the abdomen. The omentum and gubernaculum tissues were resected as they tend to envelop the coupon. Then either a control coupon or a CP coupon (1×2 cm²) was implanted in the abdominal cavity. The incision was closed in two layers. After animals were housed for 1 week (rats were monitored daily), coupons were explanted from rats. Gross observations were made including adhesion, abscess, inflammation, and encapsulation. It was found that no adhesion, abscess and inflammation associated with CP polymer coupons, but there was obvious adhesion, abscess and serious inflammation associated with implanted control polymer coupons. Coupons were retrieved with sterile surgical instruments. A swab was taken of the peritoneal cavity. Coupons were rinsed in PBS buffer to remove non-adherent cells and placed in sterile tubes for further bacteria culture. Bacteria counts obtained from cultures of control and CP coupons are shown in FIG. 9. Clearly, CP coupons show an antimicrobial effect, yielding significantly lower colony forming units (CFUs).

Example 12

Examples of biomedical articles that integrate the bioactive polymers to the polymers using described methods 1, 2, 3 below include, for example, the following articles that are in whole or in part made of polyurethane components, namely, cardiac assist devices, tissue engineering polymeric scaffolds and related devices, cardiac replacement devices, cardiac septal patches, intra aortic balloons, percutaneous cardiac assist devices, extra-corporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, syringes, o-rings, bladders, penile implants, drug delivery systems, drainage tubes, pacemaker lead insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes, biosensors and bio-diagnostic substrates.

Non-biomedical articles fabricated by hereinbefore method 1) include, for example, extruded health care products, bio-reactor catalysis beds or affinity chromatography column packings, or a biosensor and bio-diagnostic substrates.

Non-medical applications that are exemplified by method 2) include fibre membranes for water purification.

Non-medical applications of the type exemplified by method 3) include varnishes with biological function for aseptic surfaces.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The invention claimed is:

1. A method for synthesizing a pharmaceutically-active polymer, said method comprising reacting a biological coupling agent with a prepolymer in a step growth polymerization reaction, wherein said biological coupling agent has the general formula (III):

PBio-LINK A-PBio        (III), wherein PBio comprises a radical of a biologically active agent linked to LINK A through a hydrolysable covalent bond and having at least one functional group to permit step growth polymerization with said prepolymer; and LINK A is a coupled central flexible linear first segment of <2000 theoretical molecular weight formed from a diol or diamine and linked to each of said PBio fragments, wherein each PBio bears an equivalent functional group selected from hydroxyl, a primary amine, and secondary amine for polymerization with said prepolymer, and wherein said prepolymer is described by the formula:

$Y_n$-LINK B wherein
(a) $Y_n$ is [LINK B-OLIGO]$_n$;
(b) LINK B is a coupled second segment formed from a difunctional molecule selected from a diamine, diisocyanate, disulfonic acid, dicarboxylic acid, diacid chloride, and dialdehyde and having a molecular weight of 60 to 2000 Daltons linking one OLIGO to another OLIGO and an OLIGO to said biological coupling agent;
(c) OLIGO is a polymer segment having a molecular weight of less than 5,000 Daltons and comprising less than 100 monomeric repeating units; and
(d) n is an integer from 2-50, and
wherein said biologically active agent is an antimicrobial agent selected from Ciprofloxacin and Norfloxacin; an antiflammatory agent selected from Amfenac, Aceclofenac, Oxacepro and Enoxolone; an antithrombic agent selected from Bromofenac, Tirofiban and Lotrafiban; or an antiproliferation agent selected from Acivicin and Alkeren.

2. The method of claim 1, wherein LINK A is linked to PBio by carboxylic ester, amide, or sulfonamide links.

3. The method of claim 1, wherein LINK A has a molecular weight selected from 60-700 Daltons.

4. The method of claim 1, wherein said step growth polymerization reaction forms a polyester, polyamide, polyurethane, or polysulfonamide.

5. The method of claim 1, wherein LINK A is formed from a diol or diamine selected from ethylene glycol; butane diol; hexane diol; hexamethylene diol; 1,5 pentanediol; 2,2-dimethyl-1,3 propanediol; 1,4-cyclohexane diol; 1,4-cyclohexanedimethanol; tri(ethylene glycol); poly(ethylene oxide) diamine; lysine esters; silicone diols; carbonate diols; ethylene diamine; hexamethylene diamine; 1,2-diamino-2methylpropane; 3,3,-diamino-N-methyldipropylamine; 1,4 diaminobutane; 1,7 diaminoheptane; and 1,8 diaminooctane.

6. The method of claim 1, wherein LINK B has a molecular weight selected from 60-700.

7. The method of claim 1, wherein LINK B is linked to other segments via urethanes, esters, ureas, sulfonamides, carbonates, anhydrides, or amides.

8. The method of claim 1, wherein said PBio has a molecular weight of <4000 daltons.

9. The method of claim 1, wherein said PBio has a molecular weight of <2000 daltons.

10. The method of claim 1, wherein said biologically active agent is an antimicrobial agent selected from Ciprofloxacin and Norfloxacin.

11. The method of claim 1, wherein said biologically active agent is an antiflammatory agent selected from Amfenac, Aceclofenac, Oxacepro and Enoxolone.

12. The method of claim 1, wherein said biologically active agent is an anti-thrombic agent selected from Bromofenac, Tirofiban and Lotrafiban.

13. The method of claim 1, wherein biologically active agent is an antiproliferation agent selected from Acivicin and Alkeren.

\* \* \* \* \*

UNITED STATES PATENT AND TRADEMARK OFFICE
CERTIFICATE OF CORRECTION

PATENT NO. : 8,349,309 B2  
APPLICATION NO. : 12/793475  
DATED : January 8, 2013  
INVENTOR(S) : J. P. Santerre et al.

Page 1 of 1

It is certified that error appears in the above-identified patent and that said Letters Patent is hereby corrected as shown below:

Title Page, Inventors, insert line break after inventor J. Paul Santerre;

Other Publications, Budavari, insert line break before "Coessens".

In the Specification

Column 3, Line 26, replace "urinary track" with --urinary tract--;

Line 37, replace "aminoacids" with --amino acids--.

Column 6, Line 44, replace "(1)" with --(I)--.

Column 21, Line 57, replace "enzytne" with --enzyme--.

Column 26, Line 48, replace "176.6155.4" with --176.6, 155.4--.

Column 27, Line 64, "before addition of as the water" should read --before addition as the water--.

Column 28, Line 29, replace "level (22)," with --level (22).--.

Column 30, Line 11, replace "Norfloxacin 10 weeks." with --Norfloxacin at 10 weeks--.

Column 31, Line 12, replace "inflammation associated" with --inflammation was associated--.

Signed and Sealed this  
Seventeenth Day of December, 2013

Margaret A. Focarino  
*Commissioner for Patents of the United States Patent and Trademark Office*